(12) United States Patent
Mullah et al.

(10) Patent No.: US 11,535,885 B2
(45) Date of Patent: Dec. 27, 2022

(54) QUENCHER AND REPORTER DYE COMBINATIONS

(71) Applicant: LIFE TECHNOLOGIES CORPORATION, Carlsbad, CA (US)

(72) Inventors: Khairuzzaman Bashar Mullah, Union City, CA (US); Brian Evans, Mountain View, CA (US); Scott C. Benson, Alameda, CA (US); Chu-An Chang, Castro Valley, CA (US); Xiongwei Yan, Dublin, CA (US)

( * ) Notice: Subject to any disclaimer, the term of this patent is extended or adjusted under 35 U.S.C. 154(b) by 0 days.

(21) Appl. No.: 15/733,557

(22) PCT Filed: Mar. 1, 2019

(86) PCT No.: PCT/US2019/020363
§ 371 (c)(1),
(2) Date: Aug. 27, 2020

(87) PCT Pub. No.: WO2019/169307
PCT Pub. Date: Sep. 6, 2019

(65) Prior Publication Data
US 2020/0407780 A1    Dec. 31, 2020

Related U.S. Application Data

(60) Provisional application No. 62/637,546, filed on Mar. 2, 2018.

(51) Int. Cl.
*C12Q 1/68* (2018.01)
*C12Q 1/6818* (2018.01)
*C12Q 1/686* (2018.01)

(52) U.S. Cl.
CPC ........... *C12Q 1/6818* (2013.01); *C12Q 1/686* (2013.01); *C12Q 2535/122* (2013.01); *C12Q 2537/143* (2013.01); *C12Q 2565/1015* (2013.01)

(58) Field of Classification Search
CPC ...... C12Q 1/6818; C12Q 1/686; C09B 23/06; C09B 23/08; C09B 11/24; C07H 21/00
See application file for complete search history.

(56) References Cited

U.S. PATENT DOCUMENTS 6,399,392 B1 *  6/2002  Haugland ............... C09B 11/24
                                                436/805
8,137,616 B2     3/2012  Sagner et al.

FOREIGN PATENT DOCUMENTS

WO    WO-2016057459 A1    4/2016

OTHER PUBLICATIONS

Chiuman W., et al., "Efficient Signaling Platforms Built from a Small Catalytic DNA and Doubly Labeled Fluorogenic Substrates", Nucleic Acids Research, vol. 35, No. 2, Dec. 14, 2006 (Dec. 14, 2006), pp. 401-405, XP055577775, ISSN: 0305-1048, DOI: 10.1093/nar/gkl1056.
International Search Report and Written Opinion for Application No. PCT/US2019/020363, dated Apr. 15, 2019, 14 pages.
Sanman L.E., et al., "Bifunctional Probes of Cathepsin Protease Activity and pH Reveal Alterations in Endolysosomal pH during Bacterial Infection", Cell Chemical Biology, Elsevier, Amsterdam, NL, vol. 23, No. 7, Jul. 14, 2016 (Jul. 14, 2016), pp. 793-804, XP029653613, ISSN: 2451-9456, DOI:10.1016/J.CHEMBIOL.2016.05.019.

* cited by examiner

*Primary Examiner* — Jezia Riley
(74) *Attorney, Agent, or Firm* — Workman Nydegger; Logan Christenson; John Guynn

(57) ABSTRACT

Disclosed is a probe for use in biological assays. The probe includes a fluorescent dye bound to a quencher compound through an oligonucleotide linker. Also disclosed are methods of using the probe, such as for a polymerase chain reaction (PCR), such as in a quantitative PCR reaction (qPCR), as well as kits including the probe.

37 Claims, No Drawings

QUENCHER AND REPORTER DYE COMBINATIONS

TECHNICAL FIELD

This specification generally relates to FRET pairs comprising quencher and reporter dye combinations for biological applications including, for example, a polymerase chain reaction (PCR), such as a real-time or quantitative PCR (qPCR).

BACKGROUND

Fluorescent energy transfer (FRET) within dual-labeled oligonucleotide probes is widely used in assays for genetic analysis. FRET has been utilized to study DNA hybridization and amplification, the dynamics of protein folding, proteolytic degradation, and interactions between other biomolecules. Nucleic acid detection/amplification methods, such as in real-time polymerase chain reactions, use dual-labeled probes to detect and/or quantify target nucleic acids like specific gene sequences or expressed messenger RNA sequences. Fluorogenic probes for use in such methods are often labeled with both a reporter and a quencher moiety. In such cases, fluorescence from the reporter is unquenched when the two dyes are physically separated via hybridization of the probe to a nucleic acid template and/or via exonuclease activity which removes one of the quencher or reporter dye components from the probe.

Fluorescence resonance energy transfer is a form of molecular energy transfer (MET), a process by which energy is passed non-radioactively between a donor molecule and an acceptor molecule. FRET arises from the properties of certain chemical compounds; when excited by exposure to particular wavelengths of light, they emit light (i.e., they fluoresce) at a different wavelength. Such compounds are termed fluorophores. In FRET, energy is passed non-radioactively over a long distance (e.g., 10-100 Angstroms) between a donor molecule, which is a fluorophore, and an acceptor molecule, which is either another fluorophore or a quencher. The donor absorbs a photon and transfers this energy non-radioactively to the acceptor.

When two fluorophores whose excitation and emission spectra overlap are in close proximity, excitation of one fluorophore will cause the first fluorophore to transfer energy to the second fluorophore, causing the second fluorophore, in turn, to fluoresce. Stated differently, the excited-state energy of the first (donor) fluorophore is transferred by a resonance induced dipole-dipole interaction to the neighboring second (acceptor) fluorophore. As a result, the lifetime of the donor molecule is decreased and its fluorescence is quenched, while the fluorescence intensity of the acceptor molecule is enhanced and depolarized. When the excited-state energy of the donor is transferred to a non-fluorophore acceptor, such as a quencher, the fluorescence of the donor is quenched without subsequent emission of fluorescence by the acceptor. Pairs of molecules that can engage in FRET are termed FRET pairs. In order for energy transfer to occur, the donor and acceptor molecules must typically be in close proximity (e.g., up to 70 to 100 Angstroms).

Commonly used methods for detecting nucleic acid amplification products require that the amplified product (i.e., amplicon) be separated from unreacted primers. This is commonly achieved either through the use of gel electrophoresis, which separates the amplification product from the primers on the basis of a size differential, or through the immobilization of the product, allowing washing away of free primer. Other methods for monitoring the amplification process without separation of the primers from the amplicon have been described. Exemplary compounds used in such methods include TaqMan® probes, molecular beacons, SYBR GREEN® indicator dye, LUX primers, and others. The principal drawback to intercalator-based detection of PCR product accumulation, such as using SYBR GREEN® indicator dye, is that both specific and nonspecific products generate a signal.

Real-time systems for quantitative PCR (qPCR) were improved by probe-based, rather than intercalator-based PCR product detection. One probe-based method for detection of amplification product without separation from the primers is the 5' exonuclease PCR assay (also referred to as the TaqMan® assay or hydrolysis probe assay). This alternative method provides a real-time method for detecting only specific amplification products. During amplification, annealing of the probe, often referred to as a "TaqMan probe", to its target sequence generates a substrate that is cleaved by the 5' exonuclease activity of a DNA polymerase, such as Taq, when the enzyme extends from an upstream primer into the region of the probe. This dependence on polymerization ensures that cleavage of the probe occurs only if the target sequence is being amplified.

In general, the TaqMan probe is a non-extendable oligonucleotide attached to a fluorescent reporter dye (i.e., fluorophore) and a quencher moiety. When the TaqMan probe is intact, the reporter and quencher moieties are in close proximity, such that the quencher greatly reduces the fluorescence emitted by the reporter dye by Förster resonance energy transfer (FRET). Probe design and synthesis has been simplified by the finding that adequate quenching is observed for probes with the reporter at the 5' end and the quencher at the 3' end.

During the extension phase of PCR, if the target sequence is present, the probe anneals downstream from one of the primer sites and is cleaved by the 5' exonuclease activity of a DNA polymerase possessing such activity, such as Taq polymerase, as this primer is extended. The cleavage of the probe separates the reporter dye from quencher moiety, increasing the reporter dye signal. Cleavage further removes the probe from the target strand, allowing primer extension to continue to the end of the template strand. Thus, inclusion of the probe does not inhibit the overall PCR process. Additional reporter dye molecules are cleaved from their respective probes with each cycle, affecting an increase in fluorescence intensity proportional to the amount of amplicon produced.

The advantage of fluorogenic probes over DNA binding dyes, such as SYBR GREEN®, is that specific hybridization between probe and target is required to generate fluorescent signal. Thus, with fluorogenic probes, non-specific amplification due to mis-priming or primer-dimer artifact does not generate a signal. Another advantage of fluorogenic probes is that they can be labeled with different, distinguishable reporter dyes. By using probes labeled with different reporters, amplification of multiple distinct sequences can be detected in a single PCR reaction, often referred to as a multiplex assay.

Current analyses of cell and tissue functionality often require extracting as much information as possible from materials that are often limited. For example, samples such as tumor biopsies are difficult to collect and usually yield only a small amount of usable nucleic acid. PCR detection and measurement of a single target analyte, referred to as a singleplex assay, has been the gold standard for analyzing clinical research samples on the nucleic acid level, and has been invaluable in extending the limits of biological knowledge for more than a quarter century.

However, the limited amount of nucleic acid obtained from clinical research specimens often forces choices to be made about how best to utilize these precious samples. Furthermore, if the sample is limited, the number of loci that can be analyzed is also limited, reducing the amount of information that can be extracted from the sample. Finally, the additional time and materials required to set up multiple single-assay reactions could increase the expense of a complex project significantly.

Multiplex PCR analysis of nucleic acids, a strategy where more than one target is amplified and quantified from a single sample aliquot, is an attractive solution to these problems. In multiplex PCR, a sample aliquot is queried with multiple probes that contain fluorescent dyes in a single PCR reaction. This increases the amount of information that can be extracted from that sample. With multiplex PCR, significant savings in sample and materials can be realized. To increase the utility of this method, multiplexed PCR using several pairs of gene-specific primers and probes to amplify and measure multiple target sequences simultaneously have been developed. Multiplexing PCR provides the following advantages: 1) Efficiency: multiplexed PCR helps conserve sample material and avoid well-to-well variation by combining several PCR assays into a single reaction. Multiplexing makes more efficient use of limited samples, such as those harboring a rare target that cannot be split into multiple aliquots without compromising the sensitivity; 2) Economy: even though the targets are amplified in unison, each one is detected independently by using a gene-specific probe with a unique reporter dye to distinguish the amplifications based on their fluorescent signal. Once optimized, a multiplexed assay is more cost effective than the same assays amplified independently.

However, currently there are limitations to the number of targets that can be analyzed in a single multiplex PCR assay. The experimental design for multiplex PCR is more complicated than for single reactions. The probes used to detect individual targets must contain unique reporter dyes with distinct spectra. The settings for excitation and emission filters of real-time detection systems vary from manufacturer to manufacturer; therefore, instruments must be calibrated for each dye as part of the experiment optimization process. Thus, one limitation in the development of multiplex PCR assays is the number of fluorophores, and hence probes, that can be effectively measured in a single reaction. For example, in multiplexed PCR, signal crosstalk between different fluorescence reporters can compromise quantification or cause false positives. It is therefore essential to select fluorophores with minimal spectral overlap. Additionally, the fluorophores, and specifically, their emission and excitation spectra, must also be compatible with the PCR instrument to be used, and specifically, the band-pass specifications for each filter-set.

Additionally, it is also important to minimize signal cross-talk by using probes that quench well. When designing a fluorescent probe, it is necessary to ensure that the fluorophore and quencher pair is compatible, given the type of detection chemistry. In addition, when designing multiplexed reactions the spectral overlap between the fluorophores and quenchers for the different targets should be minimized to avoid possible cross-talk issues. Previously, one of the most common dye/quencher combination for a TaqMan probe was a FAM fluorophore with a TAMRA quencher. Today, "dark quenchers" have largely replaced fluorescent quenchers like TAMRA. Dark quenchers emit the energy they absorb from the fluorophore as heat rather than light of a different wavelength. "Dark quenchers" tend to give results with lower background, and are especially useful in a multiplex reaction where it is important to avoid emitted light from the quencher creating cross-talk signal with one of the reporter dyes. Thus, highly efficient "dark quenchers" considerably reduce background fluorescence leading to increased sensitivity and end-point signal. This is particularly useful for multiplex reactions because having several fluorophores in the same tube causes higher background fluorescence.

In general, multiplex PCR reactions have been limited to 4 probe combinations where for duplex reactions the most popular combination is FAM and HEX (JOE/VIC®); for triplex, FAM, HEX (JOE/VIC®), and Cy5 or NED, FAM, and VIC®; and for quadriplex, FAM, HEX (JOE/VIC®), Texas Red®, and Cy5 dyes, or FAM, VIC®, ABY, and JUN. Until now, most multiplex PCR instruments could take advantage of only four unique dye-quencher pairs. However, many of these instruments have the optical capability to perform higher levels of multiplexing, e.g., 5-plex and 6-plex PCR.

Thus, there is a need to provide additional probes comprising unique fluorophore/quencher combinations that allow for multiplex reactions which go beyond the use of only four spectral channels (i.e., 4-plex), such as for use in 5-plex and 6-plex multiplex PCR assays.

SUMMARY

In one aspect, provided herein is a probe that comprises a product of covalent conjugation of: a dye having a general Formula Ia, Formula Ib, Formula Ic, or Formula Id; a quencher having general Formula II; and a linker joining the dye and the quencher. In one embodiment, the linker is or includes an oligonucleotide.

Formula Ia, Ib, Ic, and Id are as follows:

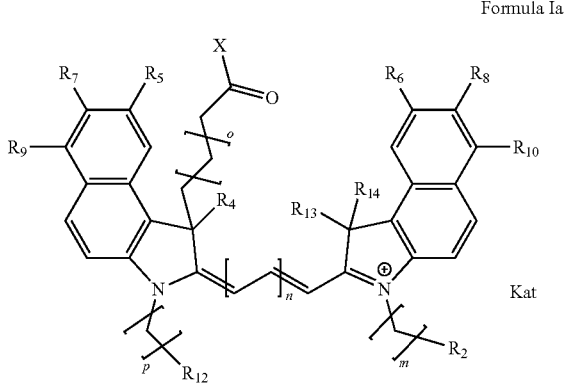

-continued

Formula Ib

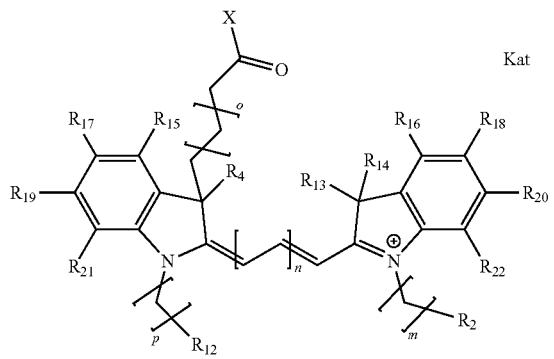

Formula Ic

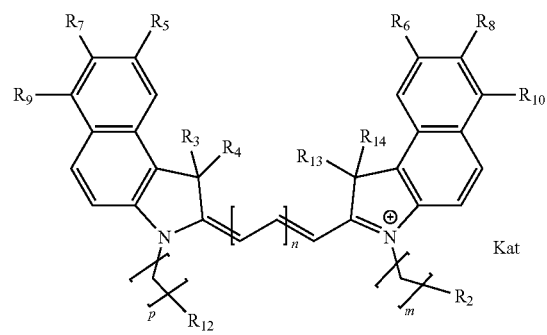

Formula Id

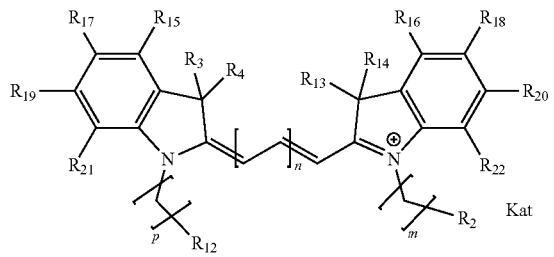

Each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof. In one embodiment, the substituted benzyl is a benzoate attached via a linker L. Each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$. Each of $R_2$ and $R_{12}$ is the same or different and is selected from the group consisting of H and $SO_3$. X is selected from the group consisting of —OH, —SH, —NH$_2$, —NH—NH$_2$, —F, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, NH(CH$_2$CH$_2$O)$_z$CH$_2$CH$_2$N$_3$, and —NR-L-NH—CO—CH$_2$—I, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom. In one embodiment, X is an azide ($N_3$)-containing group. In one embodiment, the azide-containing group comprises an aliphatic linker with a terminal azide. In one embodiment, the aliphatic linker with a terminal azide is selected from NH—CH$_2$—CH$_2$—CH$_2$—N$_3$ or NH$_2$—CH$_2$—CH$_2$—O—CH$_2$—CH$_2$—O—CH$_2$—CH$_2$—O—CH$_2$—CH$_2$—N$_3$. The above described compound further comprises a counterion, Kat, which is a number of Na$^+$, K$^+$, Ca$^{2+}$, ammonia, or other cation(s) needed to compensate the negative charge brought by the cyanine. In the Formulas, m is an integer from 0 to 5 inclusive; n is an integer from 1 to 3 inclusive; o is an integer from 0 to 12 inclusive; and p is an integer from 0 to 5 inclusive.

Formula II is as follows:

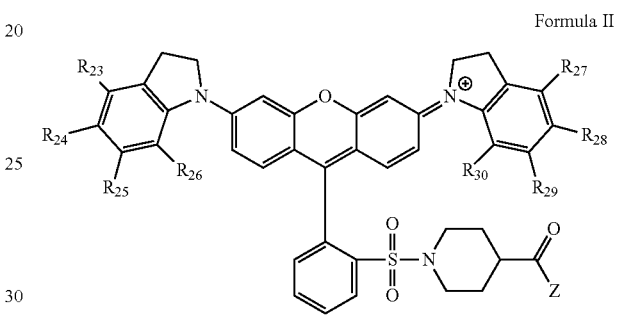

Each of $R_{23}$, $R_{24}$, $R_{25}$, $R_{26}$, $R_{27}$, $R_{28}$, $R_{29}$, and $R_{30}$ is the same or different and is independently selected from either H or $SO_3$. Z is OR, where R is H or alkyl, or NH-L, where L is

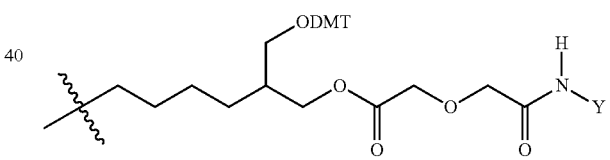

and Y is either H or a linkage to a solid support.

Another aspect provided herein is a method for conjugating or labeling a biomolecule with a dye and/or quencher using an azide-derivatized dye or quencher to label the biomolecule having a cyclooctyne moiety via a Cu-free "Click Reaction". In one embodiment, the biomolecule is an oligonucleotide. In one embodiment, the cyclooctyne moiety is dibenzocyclooctyne (DIBO). In one embodiment, the method for conjugating or labeling results in the probe as described herein.

Another aspect provided herein is a method of detecting or quantifying a target nucleic acid molecule in a sample by polymerase chain reaction (PCR), such as by quantitative real-time polymerase chain reaction (qPCR). In one embodiment, the method includes: (i) contacting a sample comprising one or more target nucleic acid molecules with a) at least one probe, such as those described herein, being sequence specific for the target nucleic acid molecule, where the at least one probe undergoes a detectable change in fluorescence upon amplification of the one or more target nucleic acid molecules; and with b) at least one oligonucleotide primer pair; (ii) incubating the mixture of step (i) with a DNA polymerase under conditions sufficient to amplify one or more target nucleic acid molecules; and (iii) detecting the presence or absence or quantifying the amount of the amplified target nucleic acid molecules by measuring fluorescence of the probe. In some embodiments, the DNA polymerase comprises 5' exonuclease activity. In some other embodiments, the DNA polymerase is a *Thermus aquaticus* (Taq) DNA polymerase. In some embodiments, the probe is a hydrolysis probe, such as a TaqMan probe.

Another aspect provided herein is a kit for PCR, such as quantitative real-time polymerase chain reaction (qPCR) and reverse transcription polymerase chain reaction (RT-PCR). In some embodiments the kit includes a probe, such as those described herein, instructions for conducting the PCR, and one or more of the following: a buffering agent, deoxynucleotide triphosphates (dNTPs), an organic solvent, an enzyme, enzyme cofactors, and an enzyme inhibitor. In another embodiment, the kit for PCR comprises the described dye and/or quencher moiety, instructions for conjugating or labeling the dye and/or quencher moiety to a biomolecule, such as an oligonucleotide, instructions for conducting the PCR, and one or more of the following: a buffering agent, deoxynucleotide triphosphates (dNTPs), an organic solvent, an enzyme, enzyme cofactors, and an enzyme inhibitor.

In yet further aspects provided herein are compositions, such as a "master mix" for PCR comprising the described probe along with other components that are used in PCR. In some embodiments, the master mix is prepared such that it requires less than a 3× dilution prior to use in PCR, e.g., 2× dilution, 1.5× dilution, 1.2× dilution, etc.

DETAILED DESCRIPTION

The hydrolysis probe assay exploits the 5' exonuclease activity of certain DNA polymerases, such as Taq, to cleave a labeled probe during PCR. One specific example of a hydrolysis probe is a TaqMan probe. In one embodiment, the hydrolysis probe contains a reporter dye at the 5' end of the probe and a quencher moiety at the 3' end of the probe. During the PCR reaction, cleavage of the probe separates the reporter dye and the quencher moiety, resulting in increased fluorescence of the reporter. Accumulation of PCR products is detected directly by monitoring the increase in fluorescence of the reporter dye. When the probe is intact, the close proximity of the reporter dye to the quencher moiety results in suppression of the reporter fluorescence primarily by Förster-type energy transfer (Förster, 1948; Lakowicz, 1983). During PCR, if the target of interest is present, the probe specifically anneals between the forward and reverse primer sites. The 5' to 3' nucleolytic activity of the Taq DNA polymerase cleaves the probe between the reporter and the quencher only if the probe hybridizes to the target. The probe fragments are then displaced from the target, and polymerization of the strand continues. The 3' end of the probe is blocked to prevent extension of the probe during PCR. This process occurs in sequential cycles and does not interfere with the exponential accumulation of the product.

Without being bound to these parameters, the general guideline for designing TaqMan probes and primers is as follows: design the primers as close as possible to, but without overlapping, the probe; the $T_m$ of the probe should be about 10° C. higher than the $T_m$ of the primers; select the strand that gives the probe more C than G bases; the five nucleotides at the 3' end of the primer should have no more than two G and/or C bases, and the reaction should be run on the two-step thermal profile with the annealing and extension under the same temperature of 60° C.

To facilitate understanding of this disclosure, a number of terms are defined below.

As used herein, a "sample" refers to any substance containing, or presumed to contain, nucleic acids and can include a sample of cells, a sample of tissue or a fluid sample isolated from an individual or individuals.

As used herein, "PCR", unless specifically defined, refers to either singleplex or multiplex PCR assays, and can be real time or quantitative PCR (wherein detection occurs during amplification), end-point PCR (when detection occurs at the end amplification), or reverse transcription PCR.

As used herein, the terms "nucleic acid," "polynucleotide," and "oligonucleotide" refer to primers, probes, oligomer fragments to be detected, oligomer controls and unlabeled blocking oligomers and shall be generic to polydeoxyribonucleotides (containing 2-deoxy-D-ribose), polyribonucleotides (containing D-ribose), and any other type of polynucleotide which is an N-glycoside of a purine or pyrimidine base, or modified purine or pyrimidine bases. There is no intended distinction in length between the term "nucleic acid," "polynucleotide," and "oligonucleotide," and these terms will be used interchangeably. "Nucleic acid", "DNA", "RNA", and similar terms can also include nucleic acid analogs. The oligonucleotides, as described herein, are not necessarily physically derived from any existing or natural sequence but may be generated in any manner, including chemical synthesis, DNA replication, reverse transcription or a combination thereof.

When two different, non-overlapping (or with some partial overlap) oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

As used herein, the terms "target sequence," "target nucleic acid," "target nucleic acid sequence," and "nucleic acid of interest" are used interchangeably and refer to a desired region which is to be either amplified, detected or both.

"Probe" as used herein, is a non-extendable oligonucleotide attached to a fluorescent reporter dye and a quencher moiety.

"Primer" as used herein can refer to more than one primer and refers to an oligonucleotide, whether occurring naturally or produced synthetically, which is capable of acting as a point of initiation of synthesis when placed under conditions in which synthesis of a primer extension product which is complementary to a nucleic acid strand is induced i.e., in the presence of nucleotides and an agent for polymerization such as DNA polymerase, at a suitable temperature for a sufficient amount of time and in the presence of a buffering agent. Such conditions can include, for example, the presence of at least four different deoxyribonucleoside triphosphates (such as G, C, A, and T) and a polymerization-inducing agent such as DNA polymerase or reverse transcriptase, in a suitable buffer ("buffer" includes substituents which are cofactors, or which affect pH, ionic strength, etc.), and at a suitable temperature. In some embodiments, the primer may be single-stranded for maximum efficiency in amplification. The primers herein are selected to be substantially complementary to the different strands of each specific sequence to be amplified. This means that the primers must be sufficiently complementary to hybridize with their respective strands. A non-complementary nucleotide fragment may be attached to the 5'-end of the primer, with the remainder of the primer sequence being complementary, or partially complementary, to the target region of the target nucleic acid. Commonly, the primers are complementary, except when non-complementary nucleotides may be present at a predetermined sequence location, such as a primer terminus as described.

The complement of a nucleic acid sequence as used herein refers to an oligonucleotide which, when aligned with the nucleic acid sequence such that the 5' end of one sequence is paired with the 3' end of the other, is in "antiparallel association." Complementarity need not be perfect; stable duplexes may contain mismatched base pairs or unmatched bases.

Stability of a nucleic acid duplex is measured by the melting temperature, or "$T_m$." The $T_m$ of a particular nucleic acid duplex under specified conditions is the temperature at which half of the base pairs have disassociated.

The term "complementary to" is used herein in relation to a nucleotide that can base pair with another specific nucleotide. Thus, for example, adenosine is complementary to uridine or thymidine and guanosine is complementary to cytidine.

The term "identical" means that two nucleic acid sequences have the same sequence or a complementary sequence.

"Amplification" as used herein denotes the use of any amplification procedures to increase the concentration of a particular nucleic acid sequence within a mixture of nucleic acid sequences.

"Polymerization", which may also be referred to as "nucleic acid synthesis", refers to the process of extending the nucleic acid sequence of a primer through the use of a polymerase and a template nucleic acid.

The term "label" as used herein refers to any atom or molecule which can be used to provide or aid to provide, a detectable (e.g., quantifiable) signal, and can be attached to a nucleic acid or protein. Labels may provide signals detectable by fluorescence, radioactivity, colorimetry, gravimetry, magnetism, enzymatic activity and the like. Labels that provide signals detectable by fluorescence are also referred to herein as "fluorophores" or "reporter dyes" or "dyes".

The term "adjacent" or "substantially adjacent" as used herein refers to the positioning of two oligonucleotides on its complementary strand of the template nucleic acid. The two oligonucleotides may be separated by 0 to about 60 nucleotides, e.g., 0, 1, 2, 3, 4, 5, 6, 7, 8, 9, or 10 nucleotides. The zero nucleotide gap means that the two oligonucleotides directly abut one another. In other words, the two template regions hybridized by two oligonucleotides may be contiguous, i.e. there is no gap between the two template regions. Alternatively, the two template regions hybridized by the oligonucleotides may be separated by 1 to about 60 nucleotides.

The term "overlapping" as used herein refers to the positioning of two oligonucleotides on its complementary strand of the template nucleic acid. The two oligonucleotides may be overlapping by 1 to about 40 nucleotides, e.g., about 1 to 10 nucleotides. In other words, the two template regions hybridized by oligonucleotides may have a common region which is complementary to both the oligonucleotides.

The terms "thermally cycling," "thermal cycling," "thermal cycles," or "thermal cycle" refer to repeated cycles of temperature changes from a total denaturing temperature, to an annealing (or hybridizing) temperature, to an extension temperature, and back to the total denaturing temperature. The terms also refer to repeated cycles of a denaturing temperature and an extension temperature, where the annealing and extension temperatures are combined into one temperature. A total denaturing temperature unwinds all double stranded fragments into single strands. An annealing temperature allows a primer to hybridize or anneal to the complementary sequence of a separated strand of a nucleic acid template. The extension temperature allows the synthesis of a nascent DNA strand of the amplicon. The term "single round of thermal cycling" means one round of denaturing temperature, annealing temperature and extension temperature. In a single round of thermal cycling, for example, there may be internal repeating cycles of an annealing temperature and an extension temperature. For example, a single round of thermal cycling may include a denaturing temperature, an annealing temperature (i.e., first annealing temperature), an extension temperature (i.e., first extension temperature), another annealing temperature (i.e., second annealing temperature), and another extension temperature (i.e., second extension temperature).

The terms "reaction mixture," "amplification mixture," or "PCR mixture" as used herein refer to a mixture of components necessary to amplify at least one amplicon from nucleic acid templates. The mixture may comprise nucleotides (dNTPs), a thermostable polymerase, primers, and a plurality of nucleic acid templates. The mixture may further comprise a Tris buffer, a monovalent salt, and/or $Mg^{2+}$. The working concentration range of each component is well known in the art and can be further optimized as needed by an ordinary skilled artisan.

The term "master mix" is a premixed concentrated solution that has all of the components for a real-time PCR reaction that are not sample-specific. A master mix usually contains a thermostable DNA polymerase, dNTPs, $MgCl_2$, and proprietary additives in a buffer optimized for PCR.

The terms "amplified product" or "amplicon" refer to a fragment of DNA amplified by a polymerase using a pair of primers in an amplification method such as PCR.

As defined herein, "5'→3' exonuclease activity" or "5' to 3' exonuclease activity" or "5' exonuclease activity" refers to that activity of a cleavage reaction including either a 5' to 3' exonuclease activity traditionally associated with some DNA polymerases, whereby nucleotides are removed from the 5' end of an oligonucleotide in a sequential manner, (i.e., *E. coli* DNA polymerase I has this activity whereas the Klenow fragment does not), or a 5' to 3' exonuclease activity wherein cleavage occurs to more than one phosphodiester bond (nucleotide) from the -5' end, or both, or a group of homologous 5'-3' exonucleases (also known as 5' exonucleases) which trim the bifurcated molecules, the branched DNA structures produced during DNA replication, recombination and repair. In some embodiments, such 5' exonuclease can be used for cleavage of the labeled oligonucleotide probe annealed to target nucleic acid sequence.

The following description of the reporter (or fluorescent) dyes, i.e., fluorophores, and quencher compounds provides general information regarding construction of the described probes. As described herein, the reporter dyes and quencher compounds can be covalently bound to one another through a linker. In some embodiments, the linker is or includes an oligonucleotide.

Reporter Dyes

In some embodiments, the reporter dye, also referred to as a fluorophore, may be a modified carbocyanine dye. For instance, these compounds may have at least one substituted indolium ring system wherein the substituent on the 3-carbon of the indolium ring contains a chemically reactive group or a conjugated substance. Other exemplary compounds incorporate an azabenzazolium ring moiety and at least one sulfonate moiety.

The carbocyanine dyes typically comprise two heterocyclic ring systems bound together by a polymethine linker, according to the formula:

A-BRIDGE-B where A is a first heterocyclic ring system that is a substituted benzazolium ring that optionally incorporates one or more nitrogen atoms (azabenzazolium rings), B is a second heterocyclic ring system that is a substituted benzazolium or azabenzazolium ring, and BRIDGE is a polymethine linker that is optionally substituted. The first and second ring systems and polymethine linker are optionally further substituted by a variety of substituents or are fused to additional rings that are optionally further substituted. In one aspect, the carbocyanine dye contains a chemically reactive group or a conjugated substance that is attached at carbon 3 of an indolium ring system. In one embodiment, the carbocyanine dye is further substituted one or more times by sulfo or sulfoalkyl.

By "sulfo" is meant sulfonic acid, or salt of sulfonic acid (sulfonate). Similarly, by "carboxy" is meant carboxylic acid or salt of carboxylic acid. "Phosphate," as used herein, is an ester of phosphoric acid, and includes salts of phosphate. "Phosphonate," as used herein, means phosphonic acid and includes salts of phosphonate. As used herein, unless otherwise specified, the alkyl portions of substituents such as alkyl, alkoxy, arylalkyl, alylamino, dialkylamino, trialkylammonium, or perfluoroalkyl are optionally saturated, unsaturated, linear or branched, and all alkyl, alkoxy, alkylamino, and dialkylamino substituents are themselves optionally further substituted by carboxy, sulfo, amino, or hydroxy.

In some embodiments, the A moiety has the formula:

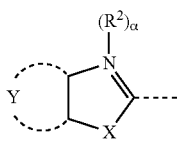

wherein Y represents the atoms necessary to form one to two fused aromatic rings having 6 atoms in each ring, which atoms are selected from —CH, —C, —CR', and —N($R^2$)$_\beta$, where each 1 is 0 or 1, and each R' is independently -L-$R_x$; or -L-$S_c$; or amino, sulfo, trifluoromethyl, or halogen; or $C_1$-$C_6$ alkyl, $C_1$-$C_6$ alkoxy, $C_1$-$C_6$ alkylamino, $C_2$-$C_{12}$ dialkylamino, optionally further substituted. Incorporation of one or more non-hydrogen substituents on the fused rings can be used to fine tune the absorption and emission spectrum of the resulting dye. In one embodiment, there is at least one non-hydrogen substituent, e.g. sulfo, an alkoxy, or halogen; the halogen is bromine in one embodiment.

In one embodiment, X is one of 0, S, Se or $NR_5$, where $R^5$ is H or an alkyl group having 1-22 carbons, that is optionally substituted one or more times by hydroxy, carboxy, sulfo, amino, alkylamino having 1-6 carbons or dialkylamino having 2-12 carbons. Alternatively, X is 0, S, or —$CR^3R^4$, where $R^3$ and $R^4$, which may be the same or different, are alkyl or arylalkyl, and optionally further substituted. In one embodiment, Each of $R_3$ and $R_4$ is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof. In one embodiment, the substituted benzyl is a benzoate attached via a linker L. For example, $R^3$ is -L-$R_x$ or -L-$S_c$ (as defined below).

In some embodiments, the substituents $R^2$, $R^4$, and $R^{12}$ are independently -L-$R_x$; or -L-$S_c$; or a $C_1$-$C_{22}$ alkyl or $C_7$-$C_{22}$ arylalkyl, each alkyl portion of which optionally incorporates up to six hetero atoms, selected from N, O and S, and each alkyl portion of which is optionally substituted one or more times by fluorine, chlorine, bromine, iodine, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium; or $R^3$ and $R^4$ taken in combination complete a five- or six-membered saturated or unsaturated ring that is substituted by -L-$R_x$; or -L-$S_c$. In some embodiments, $R^4$ is alkyl having 1-6 carbons, optionally substituted one or more times by fluorine, chlorine, bromine, iodine, hydroxy, carboxy, sulfo, or amino; e.g., $R^4$ is methyl or ethyl. In one aspect, $R^4$ is methyl. Alternatively, $R^4$ in combination with $R^{2'}$ forms a 6-membered ring, as described below; or $R^4$ taken in combination with $R^3$ forms a saturated or unsaturated ring substituent, that is substituted by -L-$R_x$ or -L-$S_c$.

In some embodiments, $R^2$ and $R^{12}$ are independently alkyl with 1-6 carbon atoms that are unsubstituted or are substituted once by hydroxy, sulfo, carboxy or amino. Where either $R^2$ or $R^{12}$ is substituted by hydroxy, sulfo, carboxy, or amino, the substituent may be separated from the indolium or other benzazolium nitrogen atom by 2-6 carbon atoms. Where $R^2$ and $R^{12}$ are unsubstituted alkyl groups, they may be methyl or ethyl. In some embodiments, $R^2$ and $R^{12}$ are methyl. Typically $R^2$ and $R^{12}$ are the same and are methyl, ethyl, sulfopropyl, or sulfobutyl.

In some embodiments, the B moiety has the formula:

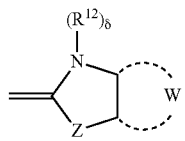

where W represents the atoms necessary to form one to two fused aromatic rings having 6 atoms in each ring, which atoms are selected from —CH, —C, —$CR^{1'}$, and —N($R^{12}$)$_{\beta'}$, where each $\beta'$ is 0 or 1, and each $R^{1'}$ is independently -L-$R_x$; or -L-$S_c$; or amino, sulfo, trifluoromethyl, or halogen; or $C_1$-$C_6$ alkyl, $C_1$-$C_6$ alkoxy, $C_1$-$C_6$ alkylamino, $C_2$-$C_{12}$ dialkylamino, each of which is optionally further substituted by carboxy, sulfo, amino, or hydroxy. Where the six membered rings form an azabenzazole ring system, they typically incorporate 1-3 nitrogen atoms or 1-2 nitrogen atoms, typically incorporated in the first 6-membered aromatic ring fused to the azole ring. In one embodiment, the ring system W contains only carbon atoms and is a benzazole ring system.

Where A or B is an azabenzazolium, the fused aromatic rings typically incorporate 1-3 nitrogen atoms or 1-2 nitrogen atoms, typically incorporated in the first 6-membered aromatic ring fused to the azole ring. Embodiments of the azabenzazole moiety include without limitation the following structures, (and the equivalent structures where the nitrogen is quaternized by $R^{12}$):

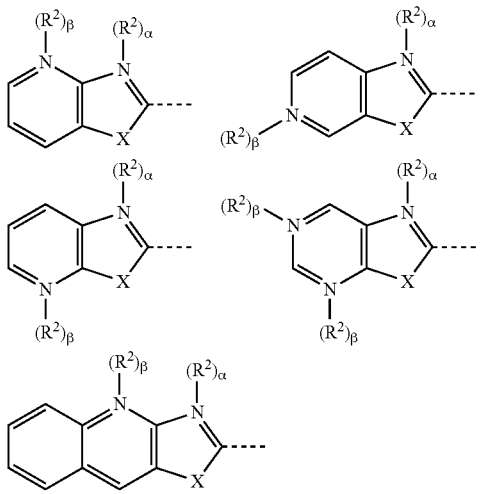

When Y or W includes a nitrogen atom, at least one of the azabenzazole nitrogen atoms is quaternized, resulting in a formal positive charge. In one embodiment, the azole nitrogen atom is quaternized, and the benzo nitrogen atom is unsubstituted. In some embodiments, the azole nitrogen atom is unsubstituted and at least one benzo nitrogen atom is quaternized. Typically, no more than one azole nitrogen on a given azabenzazole is quaternized, i.e. a is 0 or 1, β is 0 or 1, and α+ all β=1; and δ is 0 or 1, β' is 0 or 1, and δ+ all β'=1. The nitrogen atom shifts the emission spectra to a longer wavelength, relative to dyes having a carbon atom at the same position. The presence of additional fused 6-membered rings (as in the last structure above) shifts the wavelength even further.

Choice of the X and Z moieties may also affect the dye's absorption and fluorescence emission properties. X and Z are optionally the same or different, and spectral properties of the resulting dye may be tuned by careful selection of X and Z. In one embodiment, Z is one of O, S, Se or $NR^{15}$, where $R^{15}$ is H or an alkyl group having 1-22 carbons, that is optionally substituted one or more times by hydroxy, carboxy, sulfo, amino, alkylamino having 1-6 carbons, or dialkylamino having 2-12 carbons. Alternatively, Z is O, S, or $-CR^{13}R^{14}$, where $R^{13}$ and $R^{14}$, which may be the same or different, are alkyl or arylalkyl, and optionally further substituted. Typically X and Z are $-CR^3R^4$ and $-CR^{13}R^{14}$, respectively.

Where Z is $-CR^{13}R^{14}$, the substituents $R^{13}$ and $R^{14}$, which may be same or different, are independently -L-$R_x$; or -L-$S_c$; or a $C_1$-$C_{22}$ alkyl or $C_7$-$C_{22}$ arylalkyl, each alkyl portion of which optionally incorporates up to six hetero atoms, selected from N, O, and S, and each alkyl portion of which is optionally substituted one or more times by fluorine, chlorine, bromine, iodine, hydroxy, carboxy, sulfo, phosphate, amino, sulfate, phosphonate, cyano, nitro, azido, $C_1$-$C_6$ alkoxy, $C_1$-$C_6$ alkylamino, or $C_2$-$C_{12}$ dialkylamino, or $C_3$-$C_{18}$ trialkylammonium. In one embodiment, each of $R_{13}$ and $R_{14}$ is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof. In one embodiment, the substituted benzyl is a benzoate attached via a linker L. Alternatively, $R^{13}$ and $R^{14}$ in combination complete a five or six membered saturated or unsaturated ring that is optionally substituted by -L-$R_x$; or -L-$S_e$; or $R^{13}$ or $R^{14}$ combines with a methine substituent to form a ring, as described below. In some embodiments, $R^{13}$ and $R^{14}$ are independently alkyl with 1-6 carbon atoms that are unsubstituted or are substituted once by hydroxy, sulfo, carboxy, or amino. Where either $R^{13}$ or $R^{14}$ is substituted by hydroxy, sulfo, carboxy, or amino, the substituent may be separated from the indolium or other benzazolium nitrogen atom by 2-6 carbon atoms in some embodiments. In one aspect, $R^{13}$ and $R^{14}$ are alkyls having 1-6 carbons, e.g., methyls. In another aspect, one of $R^{13}$ and $R^{14}$ is methyl, and the other is alkyl having 1-6 carbons that is substituted by carboxy or by sulfo or by hydroxy, or by -L-$R_x$ or -L-$S_c$.

In some embodiments, the BRIDGE moiety has the formula:

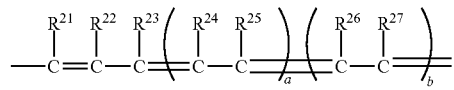

wherein a and b are independently 0 or 1. In a one aspect of the azacarbocyanine dyes, either a or b is 1, not both. The length of the polymethine bridge between the heterocyclic ring systems also affects the dye's absorption and emission properties. Where Z is $CR^{13}R^{14}$, a and b=0, and the indolium heterocycle is not fused to additional rings, the resulting "indocarbocyanine" dye typically exhibits an absorption maximum near 550 nm. Where a=1 and b=0, the "indodicarbocyanines" typically absorb maximally near 650 nm. The "indotricarbocyanine" dyes, where a and b are both 1, typically absorbs maximally near 750 nm.

Each of $R^{21}$, $R^{22}$, $R^{23}$, $R^{24}$, $R^{25}$, $R^{26}$, and $R^{27}$, when present, is independently H, F, Cl, alkyl having 1-6 carbons, alkoxy having 1-6 carbons, aryloxy, a N-heteroaromatic moiety, or an iminium ion. Alternatively, two substituents $R^{21}$, $R^{22}$, $R^{23}$, $R^{24}$, $R^{25}$, $R^{26}$, and $R^{27}$, when taken in combination, form a 4-, 5-, or 6-membered saturated or unsaturated hydrocarbon ring that is unsubstituted or is optionally substituted one or more times by a saturated or unsaturated alkyl having 1-6 carbons, halogen, or a carbonyl oxygen. In yet another embodiment, $R^{21}$ combines with $R^4$ to form a 6-membered ring that is optionally substituted by alkyl having 1-6 carbons. Alternatively, $R^{23}$ (where a and b are both 0), $R^{25}$ (where a=1 and b=0), or $R^{26}$ (where a and b are both 1) taken in combination with one of $R^{13}$ and $R^{14}$ forms a 6-membered ring that is optionally substituted by alkyl having 1-6 carbons.

Typically, each of $R^{21}$, $R^{22}$, $R^{23}$, $R^{24}$, $R^{25}$, $R^{26}$, and $R^{27}$, when present, is H. Where one of $R^{21}$, $R^{22}$, $R^{23}$, $R^{24}$, $R^{25}$, $R^{26}$, and $R^{27}$ is nonhydrogen, it is typically the substituent on the center carbon of BRIDGE, i.e., $R^{22}$ where a=0 and b=0, $R^{23}$ were a=1 and b=0, and $R^{24}$ where a=1 and b=1. Similarly, where BRIDGE incorporates a 4-, 5-, or 6-membered ring, it typically occurs at the center of the BRIDGE moiety, for instance as shown below for a pentamethine dye:

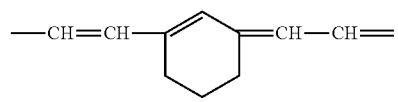

One embodiment is a compound of the formula:

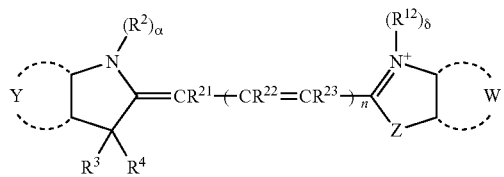

and its salts, where $R^2$, $R^3$, $R^4$, $R^{12}$, α, δ, W, Y, and Z are as defined previously. For simplicity, $R^{21-23}$ are independently as defined previously for $R^{21-27}$, and n=1, 2, or 3. Where n is >3, the dyes have spectra even further shifted into the infrared region.

Another embodiment of the dye has the formula:

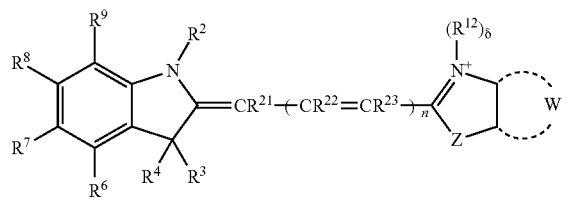

The substituents $R^6$-$R^9$ are independently selected from H, alkyl having from 1-6 carbons, alkoxy having 1-6 carbons, amino, alkylamino having 1-6 carbons, or dialkylamino having 2-12 carbons, sulfo, carboxy, perfluoroalkyl having 1-6 carbons, or halogen.

In one aspect, both A and B are benzazolium rings, according to the formula:

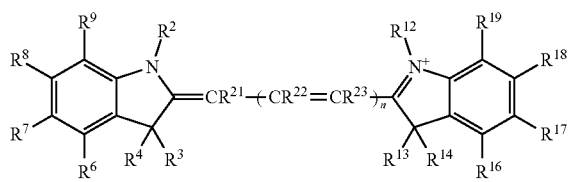

where the substituents $R^{16}$-$R^{19}$ are independently selected from H, alkyl having from 1-6 carbons, alkoxy having 1-6 carbons, amino, alkylamino having 1-6 carbons, or dialkylamino having 2-12 carbons, sulfo, carboxy, perfluoroalkyl having 1-6 carbons, or halogen.

Incorporation of one or more non-hydrogen substituents on either or both benzazolium rings are useful to fine-tune the absorption and emission spectrum. There is typically at least one non-hydrogen substituent on each of the benzazolium rings, e.g., sulfo, an alkoxy, or a halogen substituent. Typically, the substituents on the benzo rings are H or sulfo. In one embodiment, one of $R^6$, $R^7$, $R^8$, and $R^9$, or one of $R^{16}$, $R^{17}$, $R^{18}$, and $R^{19}$ is a dialkylamino that is a saturated 5- or 6-membered nitrogen heterocycle, such as piperidine. Additionally, any two adjacent substituents of $R^6$-$R^9$ and $R^{16}$—$R^{19}$ are optionally taken in combination to form one or more fused aromatic rings. These additional rings are optionally further substituted as described above for $R^6$-$R^9$ and $R^{16}$—$R^{19}$, and in particular by sulfonic acids.

Selected examples of embodiments of the carbocyanine dyes possessing additional fused aromatic rings are given below (for simplicity, all but a few of the possible substituents are shown as hydrogen, with the shortest polymethine bridge):

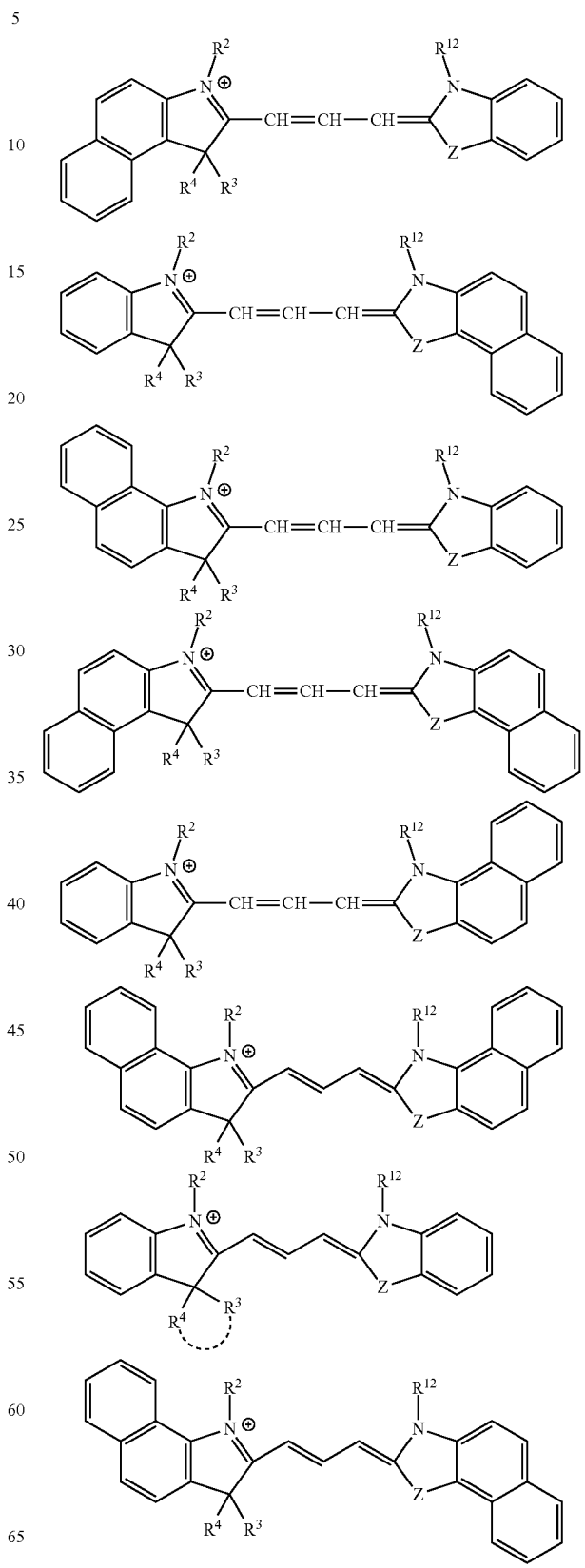

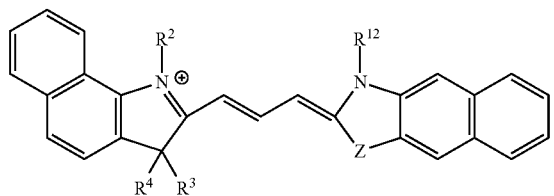

These basic structures, and their longer-wavelength analogs, are optionally further substituted as described in this section. Additional variants not specifically depicted above are also within the scope of this disclosure.

In one aspect, the carbocyanine dyes are sulfonated one or more times. If the dye is substituted by sulfo, it may be sulfonated at $R^7$ or $R^{17}$ or both, or sulfoalkylated at $R^2$ or $R^{12}$ or both, or is both sulfonated and sulfoalkylated. Typically, where the aromatic ring of Y or W contains one or more nitrogen atoms, the ring is not sulfonated. Generally, commercially available reactive carbocyanine dyes are sulfonated up to three times (at positions corresponding to $R^7$ and $R^{17}$, and as sulfoalkyl at one of $R^2$ and $R^{12}$), leaving one of $R^2$ and $R^{12}$ for the location of the reactive group. In contrast, by attaching the reactive group (or conjugated substance) at $R^3$, certain embodiments of the carbocyanine dyes may be sulfonated at least four times (at $R^7$, at $R^{1'}$, and as sulfoalkyl at $R^2$ and $R^{12}$). This extra sulfonation, as well as the change in attachment site, results in reactive dyes and dye conjugates that are brighter, more soluble in aqueous solutions, and more resistant to the fluorescence quenching that results from dye-dye stacking interactions. However, sulfonation by four or more sulfonic acids is not required for the dyes to have spectral properties that are superior to those of structurally similar dyes that are not linked through the 3 position of the indolium ring.

In addition, certain embodiments of the dyes are substituted by one or more chemically reactive groups (-L-$R_x$) or conjugated substances (-L-$S_c$), as described below. Typically, the -L-$R_x$ or -L-$S_c$ moieties are bound to the dye at an $R^2$, $R^3$, $R^4$, $R^{13}$, or $R^{14}$. Alternatively, -L-$R_x$ or -L-$S_c$ may be bound to the dye at an aromatic carbon atom of the azabenzazolium ring, or the benzazolium ring. In an embodiment, one or more of $R^2$ and $R^{12}$ is -L-$R_x$ or -L-$S_c$. In yet another embodiment, one or more of $R^3$, $R^4$, $R^{13}$, and $R^{14}$ is -L-$R_x$ or -L-$S_c$. Alternatively, one or more of $R^{21}$, $R^{22}$, $R^{23}$, $R^{24}$, $R^{25}$, $R^{26}$, and $R^{27}$ is -L-$R_x$ or -L-$S_c$. In one embodiment, the dye is substituted by only one -L-$R_x$ or -L-$S_c$.

Exemplary fluorescent dyes include, but are not limited to:

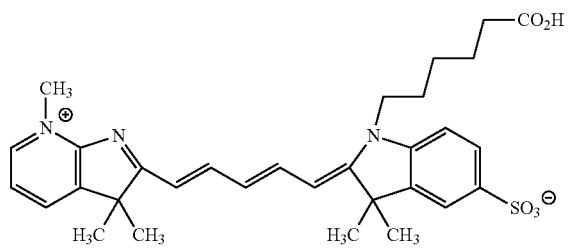

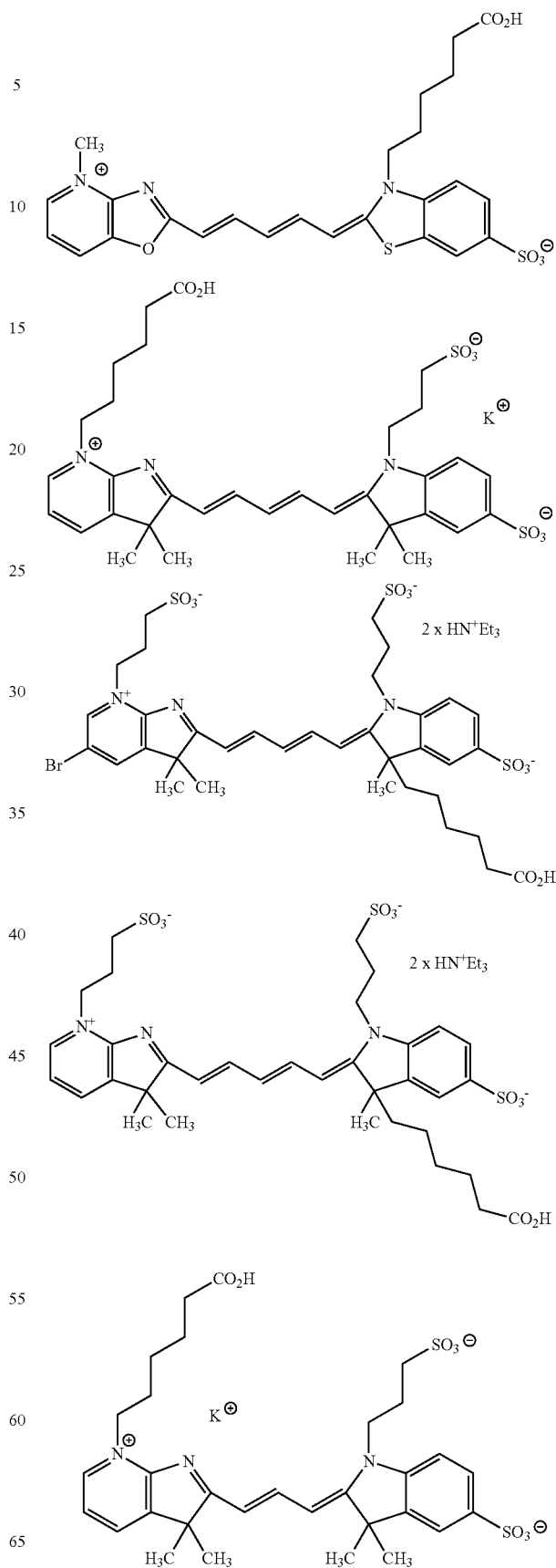

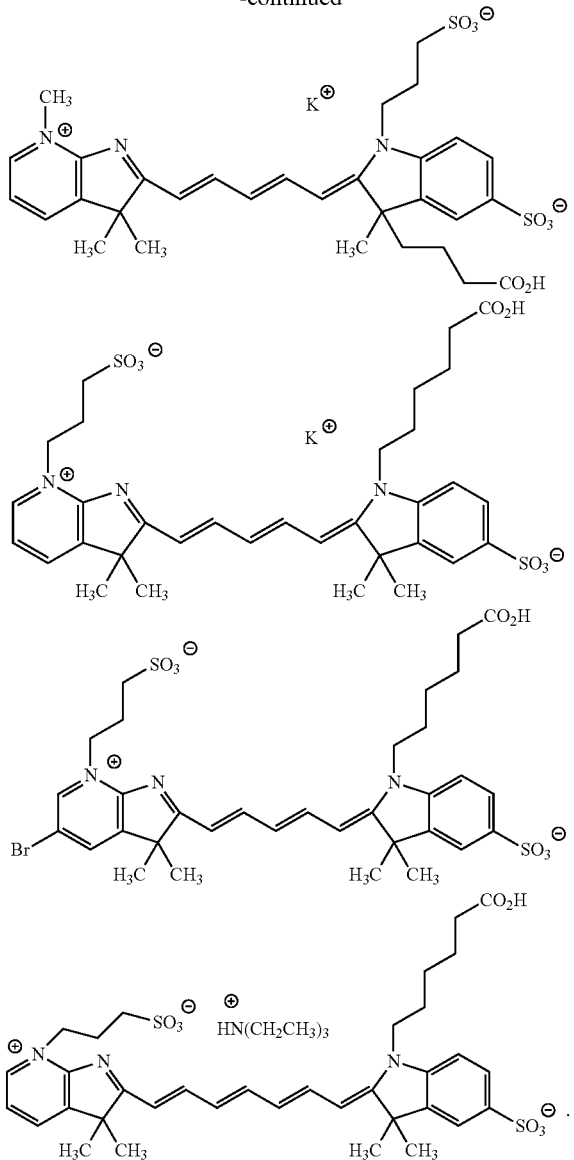

Many embodiments of the compounds possess an overall electronic charge. It is to be understood that when such electronic charges are shown to be present, they are balanced by the presence of an appropriate counterion Kat, which may or may not be explicitly identified. A biologically compatible counterion is not toxic in biological applications and does not have a substantially deleterious effect on biomolecules. Where the compound is positively charged, the counterion is typically selected from, but not limited to, chloride, bromide, iodide, sulfate, alkanesulfonate, arylsulfonate, phosphate, perchlorate, tetrafluoroborate, tetraarylboride, nitrate and anions of aromatic or aliphatic carboxylic acids. Where the compound is negatively charged, the counterion is typically selected from, but not limited to, alkali metal ions, alkaline earth metal ions, transition metal ions, ammonium or substituted ammonium or pyridinium ions. In some embodiments, any necessary counterion is biologically compatible, is not toxic as used, and does not have a substantially deleterious effect on biomolecules. Counterions are readily changed by methods well known in the art, such as ion-exchange chromatography, or selective precipitation.

It is to be understood that the dyes as disclosed herein have been drawn in one or another particular electronic resonance structure. Every aspect discussed above applies equally to dyes that are formally drawn with other permitted resonance structures, as the electronic charge on the subject dyes are delocalized throughout the dye itself.

In one embodiment, the dye includes multiple sulfonate groups. In some embodiments, the dye includes a reactive functional group or a protected version thereof for linking the dye to another substance. In some embodiments, the dye is provided in a protected form, e.g., as a phosphoramidite derivative which can be used to conjugate the dye to a molecule, such as an oligonucleotide during automated nucleic acid synthesis, as is known in the art. Representative carbocyanine dye structures as described herein are shown below.

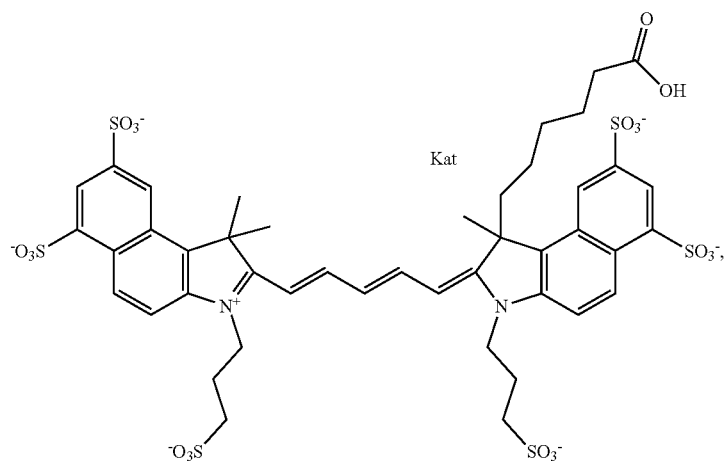

-continued
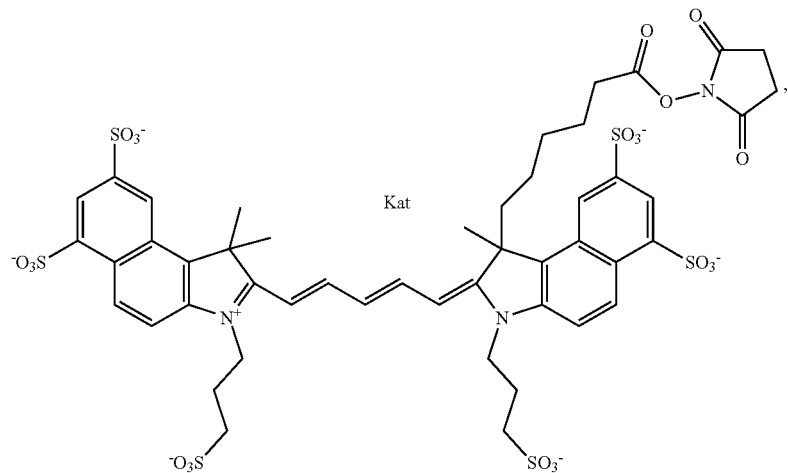
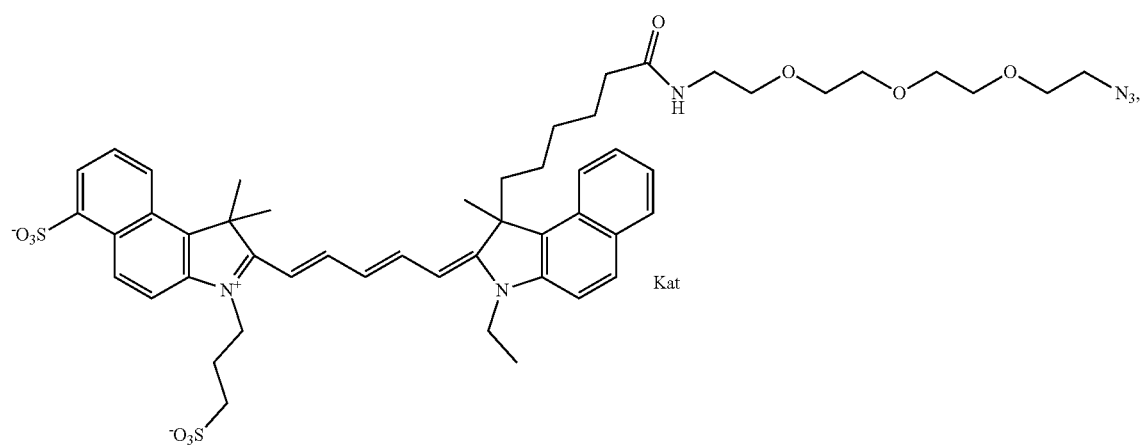
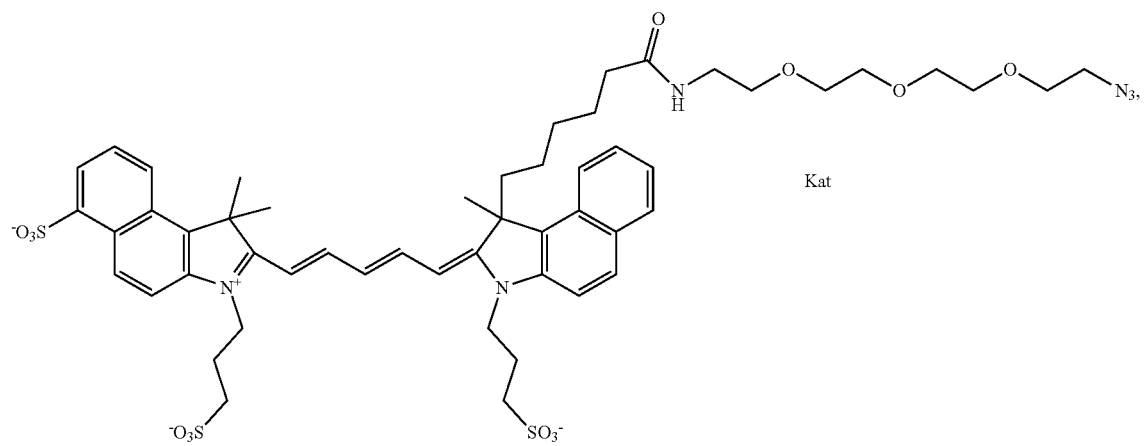

-continued
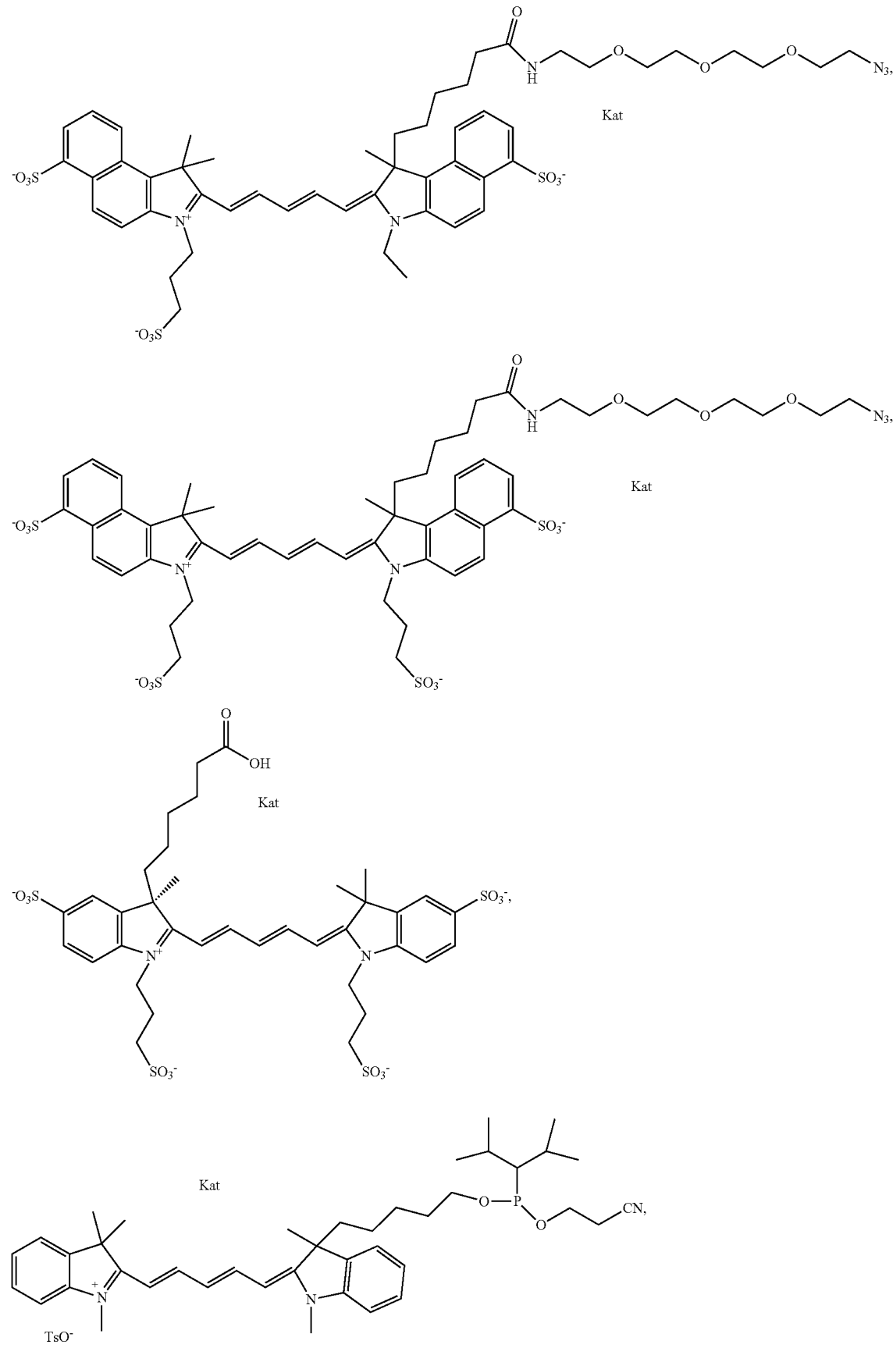

-continued

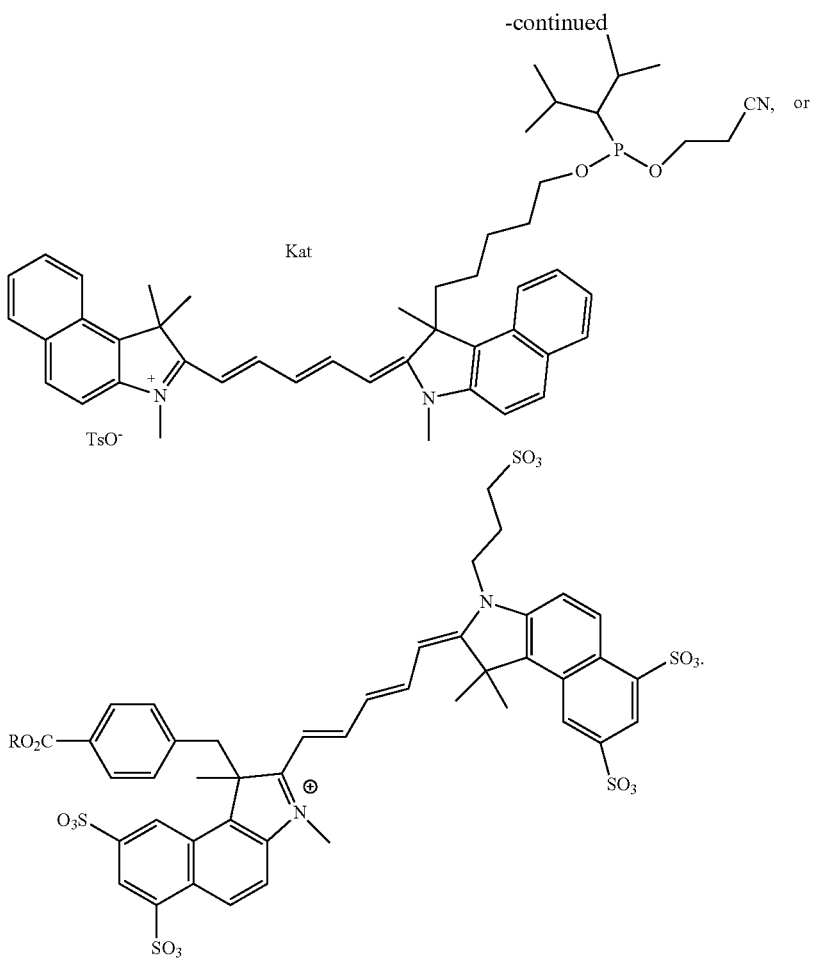

Conjugates of Reactive Dyes

In one embodiment, the dye contains at least one group -L-$R_x$, where $R_x$ is a reactive group that is attached to the dye by a covalent linkage L. In certain embodiments, a covalent linkage attaching the dye to $R_x$ contains multiple intervening atoms that serve as a spacer. The dyes with a reactive group ($R_x$) label a wide variety of organic or inorganic substances that contain or are modified to contain functional groups with suitable reactivity, resulting in chemical attachment of the conjugated substance (Se), represented by -L-$S_c$.

As used herein, "reactive group" means a moiety on the compound that is capable of chemically reacting with a functional group on a different compound to form a covalent linkage. Typically the reactive group is an electrophile or nucleophile that can form a covalent linkage through exposure to the corresponding functional group that is a nucleophile or electrophile, respectively. Alternatively, the reactive group is a photoactivatable group, and becomes chemically reactive only after illumination with light of an appropriate wavelength. Typically, the conjugation reaction between the reactive dye and the substance to be conjugated results in one or more atoms of the reactive group $R_x$ to be incorporated into a new linkage L attaching the dye to the conjugated substance $S_c$. Selected examples of reactive groups and linkages are shown below in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |

TABLE 1-continued

Examples of some routes to useful covalent linkages

| Electrophilic Group | Nucleophilic Group | Resulting Covalent Linkage |
|---|---|---|
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

*Activated esters, as understood in the art, generally have the formula —COΩ, where Ω is a good leaving group (e.g. succinimidyloxy (—OC4H4N3); sulfosuccinimidyloxy (—OC4H3O2SO3H), -1-oxybenzotriazolyl (—OC6H4N3); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCORa or —OCNRaNHRb, where Ra and Rb, which may be the same or different, are C1-C6 alkyl, C1-C6 perfluoroalkyl, or C1-C8 alkoxy; or cyclohexyl, 3-dimethylaminopropyl, or N-morpholinoethyl).
**Acyl azides can also rearrange to isocyanates The covalent linkage L binds the reactive group $R_x$ or conjugated substance $S_c$ to the compound, either directly (L is a single bond) or with a combination of stable chemical bonds, optionally including single, double, triple or aromatic carbon-carbon bonds, as well as carbon-nitrogen bonds, nitrogen-nitrogen bonds, carbon-oxygen bonds, carbon-sulfur bonds, phosphorus-oxygen bonds, phosphorus-nitrogen bonds, and nitrogen-platinum bonds. L typically includes ether, thioether, carboxamide, sulfonamide, urea, urethane or hydrazine moieties. Exemplary L moieties have 1-20 nonhydrogen atoms selected from the group consisting of C, N, O, P, and S and are composed of any combination of ether, thioether, amine, ester, carboxamide, sulfonamide, hydrazide bonds and aromatic or heteroaromatic bonds. In some embodiments, L is a combination of single carbon-carbon bonds and carboxamide or thioether bonds. The longest linear segment of the linkage L may contain 4-10 nonhydrogen atoms, including one or two heteroatoms. Examples of L include substituted or unsubstituted polymethylene, arylene, alkylarylene, arylenealkyl, or arylthio. In one embodiment, L contains 1-6 carbon atoms; in another, L comprises a thioether linkage. In yet another embodiment, L is or incorporates the formula $-(CH_2)_d(CONH(CH_2)_e)_{z'}-$, or $-(CH_2)_d(CON(CH_2)_4NH(CH_2)_e)_{z'}-$, $-(CH_2)_d(CONH(CH_2)_cNH_2)_{z'}-$, $-(CH_2)_d(CONH(CH_2)_eNHCO)_{z'}-$, where d is 0-5, e is 1-5, and z' is 0 or 1.

Choice of the reactive group used to attach the dye to the substance to be conjugated typically depends on the functional group on the substance to be conjugated and the type or length of covalent linkage desired. The types of functional groups typically present on the organic or inorganic substances include, but are not limited to, amines, amides, azides, thiols, alcohols, phenols, aldehydes, ketones, phosphates, imidazoles, hydrazines, hydroxylamines, disubstituted amines, halides, epoxides, carboxylate esters, sulfonate esters, purines, pyrimidines, carboxylic acids, olefinic bonds, or a combination of these groups. A single type of reactive site may be available on the substance (typical for polysaccharides), or a variety of sites may occur (e.g., amines, thiols, alcohols, phenols), as is typical for proteins. A conjugated substance may be conjugated to more than one dye, which may be the same or different, or to a substance that is additionally modified by a hapten, such as biotin. Although some selectivity can be obtained by careful control of the reaction conditions, selectivity of labeling is best obtained by selection of an appropriate reactive dye.

Typically, $R_x$ will react with an amine, a thiol, an alcohol, an aldehyde or a ketone. In some embodiments, $R_x$ reacts with an amine or a thiol functional group. In one embodiment, $R_x$ is an acrylamide, a reactive amine (including a cadaverine or ethylenediamine), an activated ester of a carboxylic acid (typically a succinimidyl ester of a carboxylic acid), an acyl azide, an acyl nitrile, an aldehyde, an alkyl halide, an anhydride, an aniline, an aryl halide, an azide, an aziridine, a boronate, a carboxylic acid, a diazoalkane, a haloacetamide, a halotriazine, a hydrazine (including hydrazides), an imido ester, an isocyanate, an isothiocyanate, a maleimide, a phosphoramidite, a sulfonyl halide, or a thiol group.

Where $R_x$ is an activated ester of a carboxylic acid, the reactive dye may be useful for preparing dye-conjugates of proteins, nucleotides, oligonucleotides, or haptens. Where $R_x$ is a maleimide or haloacetamide, the reactive dye may be useful for conjugation to thiol-containing substances.

In some embodiments, $R_x$ is a carboxylic acid, a succinimidyl ester of a carboxylic acid, a haloacetamide, a hydrazine, an isothiocyanate, a maleimide group, an aliphatic amine, a perfluorobenzamido, an azidoperfluorobenzamido group, or a psoralen. In some embodiments, $R_x$ is a succinimidyl ester of a carboxylic acid, a maleimide, or an iodoacetamide. In an embodiment, $R_x$ is a succinimidyl ester of a carboxylic acid.

In some embodiments, $R_x$ comprises an azide, and the strain-promoted azide-alkyne click reaction is employed, which provides a selective, bioorthogonal, and catalyst-free ligation between an azide and a strained cyclic alkyne, such as dibenzocyclooctyne.

In some embodiments, $S_c$ is a nucleic acid base, nucleoside, nucleotide, or a nucleic acid polymer, including those that are modified to possess an additional linker or spacer for attachment of the dyes, such as an alkynyl linkage, an aminoallyl linkage, or a heteroatom-substituted linker, or other linkage.

In another embodiment, the conjugated substance is a nucleoside or nucleotide analog that links a purine or pyrimidine base to a phosphate or polyphosphate moiety through a noncyclic spacer.

In another embodiment, the dye is conjugated to the carbohydrate portion of a nucleotide or nucleoside, typically through a hydroxyl group but perhaps also through a thiol or amino group. Typically, the conjugated nucleotide is a nucleoside triphosphate or a deoxynucleoside triphosphate or a dideoxynucleoside triphosphate. Incorporation of methylene moieties or nitrogen or sulfur heteroatoms into the phosphate or polyphosphate moiety may also be useful.

Nonpurine and nonpyrimidine bases such as 7-deazapurines and nucleic acids containing such bases can also be coupled to dyes. Nucleic acid adducts prepared by reaction of depurinated nucleic acids with amine, hydrazide or hydroxylamine derivatives provide an additional means of labeling and detecting nucleic acids.

In some embodiments, nucleic acid polymer conjugates are labeled, single- or multi-stranded, natural or synthetic DNA or RNA, DNA or RNA oligonucleotides, or DNA/RNA hybrids, or incorporate an unusual linker such as morpholine derivatized phosphates (AntiVirals, Inc., Corvallis Oreg.), or peptide nucleic acids such as N-(2-aminoethyl)glycine units. When the nucleic acid is a synthetic oligonucleotide, it typically contains fewer than 50 nucleotides, more typically fewer than 25 nucleotides. Conjugates of peptide nucleic acids (PNA) may be used for some applications because of their generally faster hybridization rates.

In another embodiment, fluorescent nucleic acid polymers can be prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. In this embodiment, fluorescent RNA polymers are typically prepared from labeled nucleotides by transcription. Typically, the dye is attached via one or more purine or pyrimidine bases through an amide, ester, ether or thioether bond; or is attached to the phosphate or carbohydrate by a bond that is an ester, thioester, amide, ether or thioether. Alternatively, a dye conjugate may be simultaneously labeled with a hapten, such as biotin or digoxigenin, or to an enzyme such as alkaline phosphatase, or to a protein such as an antibody. Nucleotide conjugates are readily incorporated by DNA polymerase and can be used for in situ hybridization and nucleic acid sequencing.

In another aspect, the oligonucleotide may incorporate an aliphatic amine, which may be subsequently conjugated to an amine-reactive dye or a thiol or thiophosphate, which in turn may be conjugated to a thiol-reactive dye.

In one embodiment, conjugates of biological polymers such as oligonucleotides and nucleic acid polymers are also labeled with at least a second fluorescent or nonfluorescent dye to form an energy-transfer pair. In one embodiment, the second nonfluorescent dye is a quencher. In some aspects, the labeled conjugate functions as an enzyme substrate, and enzymatic hydrolysis disrupts the energy transfer. More specifically, and in one embodiment, the 5' to 3' exonuclease activity of a nucleic acid polymerase cleaves the oligonucleotide, thus releasing the fluorophore and quencher from their proximate location and thereby removing or substantially removing the quenching effect on the fluorophore by the quencher.

Quenchers

In one embodiment, a quencher is a derivative of 3- and/or 6-amino xanthenes that are substituted at one or more amino nitrogen atoms by an aromatic or heteroaromatic quenching moiety, Q. In one embodiment, the described quenching compounds typically have absorption maxima above 530 nm, have little or no observable fluorescence and efficiently quench a broad spectrum of fluorescence, such as is emitted by the fluorophores as disclosed herein. In one embodiment, the quenching compound is a substituted rhodamine. In another embodiment, the quenching compound is a substituted rhodol. In yet another embodiment, the quencher is a chemically reactive compound. Chemically reactive quenching compounds possess utility for labeling a wide variety of substances, including biomolecules, such as nucleic acids. These labeled substances are highly useful for a variety of energy-transfer assays and applications, particularly when used in combination with a fluorophore.

As used herein, each quenching moiety, Q, is an aromatic or heteroaromatic ring system, having 1-4 fused aromatic or heteroaromatic rings, attached to the amino nitrogen by a single covalent bond. Where the Q moiety is fully aromatic and contains no heteroatom, Q comprises 1~4 fused six-membered aromatic rings. Where the Q moiety is heteroaromatic, Q incorporates at least one 5- or 6-membered aromatic heterocycle that contains at least 1 and as many as 4 heteroatoms that are selected from the group consisting of O, N, and S in any combination, that is optionally fused to an additional six-membered aromatic ring, or is fused to one 5- or 6-membered heteroaromatic ring that contains at least 1 and as many as 3 heteroatoms that are selected from the group consisting of O, N, and S in any combination.

In one embodiment, each Q moiety is bound to the xanthene compounds at a 3- or 6-amino nitrogen atom via a single covalent bond. In some embodiments, the amino nitrogen substituents, taken in combination, form a 5- or 6-membered heterocycle that is a piperidine, a morpholine, a pyrrolidine, a pyrazine, or a piperazine, and the Q moiety is fused to the resulting heterocycle adjacent to the xanthene nitrogen, so as to be formally bound to the amino nitrogen via a single bond. The Q moiety may be bound to the amino nitrogen atom at either an aromatic or heteroaromatic ring, provided it is attached at a carbon atom of that ring.

Typically, the Q moieties are substituted or unsubstituted phenyl, naphthyl, anthracenyl, benzothiazole, benzoxazole, or benzimidazole. Where the amino nitrogen substituents form a 5- or 6-membered heterocycle and the Q moiety is fused to the resulting heterocycle, the heterocycle is typically a pyrrolidine ring and the Q moiety is typically a fused six-membered aromatic ring. In some embodiments, Q is a phenyl or substituted phenyl.

In various embodiments, each Q moiety is optionally and independently substituted by hydrogen, halogen, cyano, sulfo, alkali or ammonium salt of sulfo, carboxy, alkali or ammonium salt of carboxy, nitro, alkyl, perfluoroalkyl, alkoxy, alkylthio, amino, monoalkylamino, dialkylamino or alkylamido.

In one embodiment, the quenching compounds have the formula

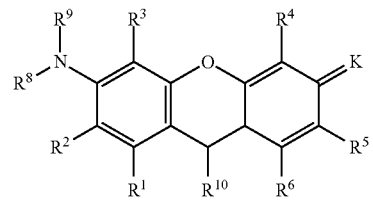

wherein the K moiety is O or $N^+R^{18}R^{19}$.

For all the quenching compounds, at least one of $R^8$, $R^9$, $R^{18}$, and $R^{19}$ is a Q moiety. Alternatively, either $R^8$ taken in combination with $R^9$, or $R^{18}$ taken in combination with IV, forms a saturated 5- or 6-membered heterocycle that is a piperidine, or a pyrrolidine that is fused to a Q moiety. Typically one of $R^8$ and $R^9$ and one of $R^{18}$ and $R^{19}$ are each a Q moiety, which are the same or different. In another embodiment, each of $R^8$, $R^9$, $R^{18}$ and $R^{19}$ is a Q moiety, which may be the same or different.

The remainder of $R^8$, $R^9$, $R^{18}$, and $R^{19}$ are independently H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl. Alternatively, where $R^8$ in combination with $R^9$, or $R^{18}$ in combination with $R^{19}$, or both, forms a saturated 5- or 6-membered heterocyclic ring that is a piperidine, a morpholine, a pyrrolidine, a pyrazine, or a piperazine, that is optionally substituted by methyl, sulfonic acid, a salt of sulfonic acid, carboxylic acid, a salt of carboxylic acid, or a carboxylic acid ester of a $C_1$-$C_6$ alkyl. Alternatively, one or more of $R^8$ in combination with $R^2$, $R^9$ in combination with $R^3$, $R^{18}$ in combination with $R^4$, or $R^{19}$ in combination with $R^5$, forms a 5- or 6-membered ring that is saturated or unsaturated, and that is optionally substituted by one or more $C_1$-$C_6$ alkyls or —$CH_2SO_3X$, where X is H or a counterion.

In one embodiment, $R^1$ and $R^6$ are H, or one or more of $R'$ in combination with $R^2$, or $R^6$ in combination with $R^5$, is a fused six-membered aromatic ring.

In one embodiment, substituents $R^2$, $R^3$, $R^4$, and $R^5$ are independently H, F, Cl, Br, I, CN; or $C_1$-$C_{18}$ alkyl, or $C_1$-$C_{18}$ alkoxy, where each alkyl or alkoxy is optionally further substituted by F, Cl, Br, I, a carboxylic acid, a salt of carboxylic acid, or a carboxylic acid ester of a $C_1$-$C_6$ alcohol; or —$SO_3X$.

In one embodiment, the pendant group $R^{10}$ is H, CN, a carboxylic acid, a salt of carboxylic acid, or a carboxylic acid ester of a $C_1$-$C_6$ alcohol. Alternatively $R^{10}$ is a saturated or unsaturated, branched or unbranched $C_1$-$C_{18}$ alkyl that is optionally substituted one or more times by F, Cl, Br, carboxylic acid, a salt of carboxylic acid, a carboxylic acid ester of a $C_1$-$C_6$ alcohol, —$SO_3X$, amino, alkylamino, or dialkylamino, the alkyl groups of which have 1-6 carbons. In another embodiment, $R^{10}$ has the formula

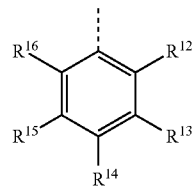

where $R^{12}$, $R^{13}$, $R^{14}$, $R^{15}$ and $R^{16}$ are independently H, F, Cl, Br, I, —$SO_3X$, a carboxylic acid, a salt of carboxylic acid, CN, hydroxy, amino, hydrazino, azido; or $C_1$-$C_{18}$ alkyl, $C_1$-$C_{18}$ alkoxy, $C_1$-$C_{18}$ alkylthio, $C_1$-$C_{18}$ alkanoylamino, $C_1$-$C_{18}$ alkylaminocarbonyl, $C_2$-$C_{36}$ dialkylaminocarbonyl, $C_1$-$C_{18}$ alkyloxycarbonyl, or $C_7$-$C_{18}$ arylcarboxamido, the alkyl or aryl portions of which are optionally substituted one or more times by F, Cl, Br, I, hydroxy, carboxylic acid, a salt of carboxylic acid, a carboxylic acid ester of a $C_1$-$C_6$ alcohol, —$SO_3X$, amino, alkylamino, dialkylamino or alkoxy, the alkyl portions of each having 1-6 carbons. Alternatively, a pair of adjacent substituents $R^{13}$ and $R^{14}$, $R^{14}$ and $R^{15}$, or $R^{15}$ and $R^{16}$, taken in combination, form a fused 6-membered aromatic ring that is optionally further substituted by carboxylic acid, or a salt of carboxylic acid.

The compounds are optionally substituted by a reactive group ($R_x$) or conjugated substance (Se) that is attached to the compound by a covalent linkage, L, as described in detail above. Typically, the compound is substituted by an -L-$R_x$ or -L-$S_e$ moiety at one or more of $R^8$, $R^9$, $R^{12}$, $R^{13}$, $R^{14}$, $R^{15}$, $R^{16}$, $R^{18}$, or $R^{19}$, e.g., at one of $R^{12}$-$R^{16}$, or at $R^{12}$, $R^{14}$ or $R^{15}$, or as a substituent on a Q moiety. Alternatively, an -L-$R_x$ or -L-$S_c$ moiety is present as a substituent on an alkyl, alkoxy, alkylthio or alkylamino substituent. In one embodiment, exactly one of $R^8$, $R^9$, $R^{12}$, $R^{13}$, $R^{14}$, $R^{15}$, $R^{16}$, $R^{18}$, or $R^{19}$ is an -L-$R_x$ or -L-Se moiety. In another embodiment, exactly one of $R^{12}$, $R^{13}$, $R^{14}$, $R^{15}$, or $R^{16}$ is an -L-$R_x$ or -L-$S_c$ moiety. In one embodiment, one of $R^{12}$, $R^{14}$, and $R^{15}$ is an -L-$R_x$ or an -L-$S_c$ moiety.

In embodiments where the K moiety is $N^+R^{18}R^{19}$, the compounds are rhodamines, and have the formula

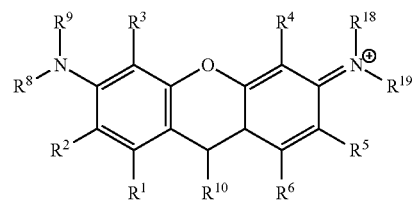

wherein at least one of $R^8$, $R^9$, $R^{18}$ and $R^{19}$ is a Q moiety. In some embodiments, at least one of $R^8$ and $R^9$ is a Q moiety and at least one of $R^{18}$ and $R^{19}$ is a Q moiety, which may be the same or different.

In embodiments where the K moiety is 0, the compounds are rhodols, and have the formula

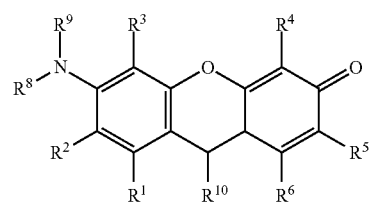

wherein at least one of $R^8$ and $R^9$ is a Q moiety.

In one embodiment, the instant compounds have the formula

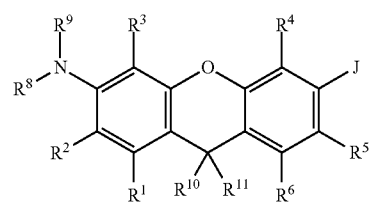

wherein J is O—$R^7$ or $NR^{18}R^{19}$, and each of $R^1$-$R^{19}$ is as defined above.

The precursors to the quenching compounds typically do not function as quenchers unless or until the aromaticity of the ring system is restored, as for the quenching compounds described above. In these precursors $R^7$ is H, $C_1$-$C_6$ alkyl, $C_1$-$C_6$ carboxyalkyl, $C_1$-$C_6$ sulfoalkyl, a salt of $C_1$-$C_6$ carboxyalkyl, or a salt of $C_1$-$C_6$ sulfoalkyl, wherein the alkyl portions are optionally substituted by amino, hydroxy, carboxylic acid, a salt of carboxylic acid, or a carboxylic acid ester of a $C_1$-$C_6$ alkyl. Alternatively, $R^7$ is a monovalent radical formally derived by removing a hydroxy group from a carboxylic acid, a sulfonic acid, a phosphoric acid, or a mono- or polysaccharide, such as a glycoside.

In one embodiment, $R^{10}$ is as defined previously, and $R^{11}$ is H, hydroxy, CN or alkoxy having 1-6 carbons. Alternatively, $R^{10}$ in combination with $R^{11}$ forms a 5- or 6-membered spirolactone ring, or $R^{11}$ in combination with $R^{12}$ forms a 5- or 6-membered spirolactone ring, or a 5- or 6-membered sulfone ring.

These precursor compounds are readily converted to the fully conjugated quenching compounds by chemical, enzymatic, or photolytic means. Typically, the colorless precursors are substituted by an -L-$R_x$ moiety, or are conjugated to a desired substance (Se).

Exemplary quencher compounds include, but are not limited to, the following:

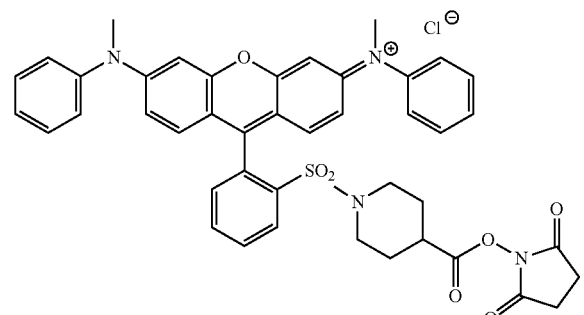

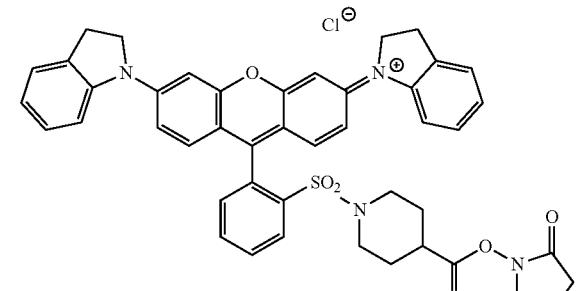

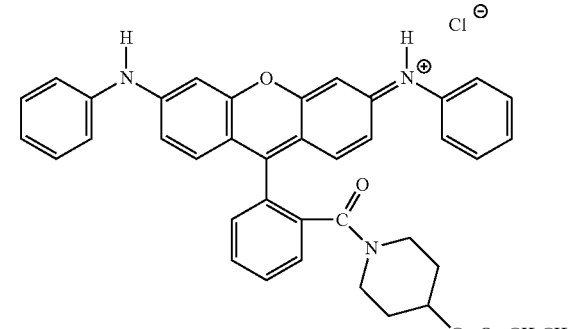

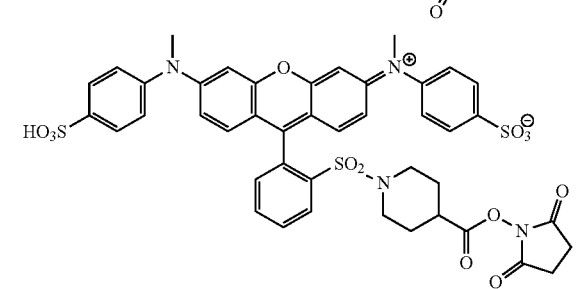

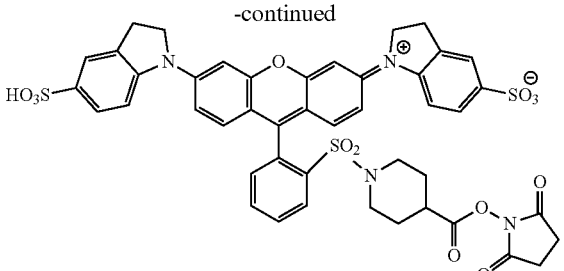

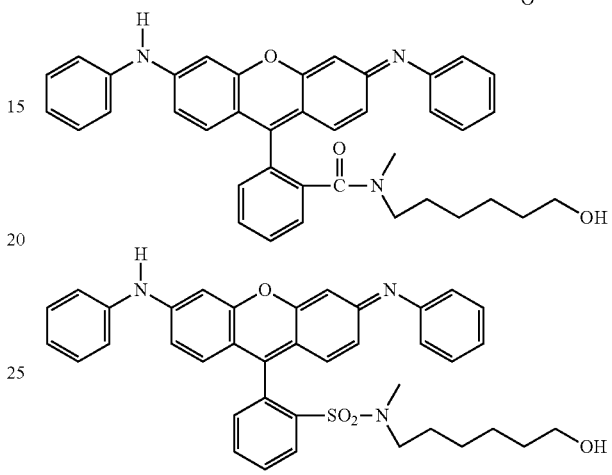

In one embodiment, the quencher is

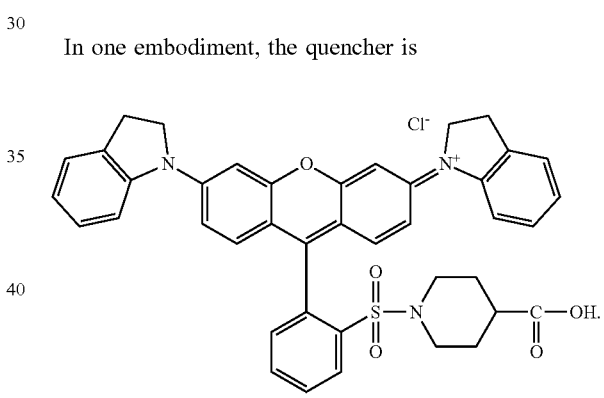

In one embodiment, the quencher includes one or more sulfonate or $SO_3H$ substituents, such as, e.g.,

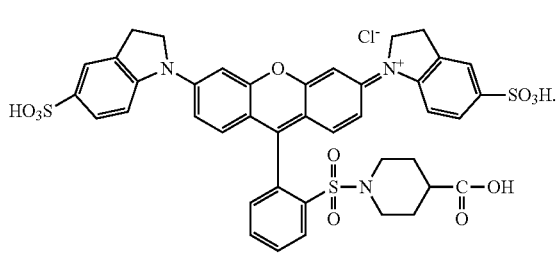 [SMILES: O=C(O)C1CCN(S(=O)(=O)c2ccccc2-c2c3cc/c(=[N+]4/CCc5cc(S(=O)(=O)O)ccc54)cc-3oc3cc(N4CCc5cc(S(=O)(=O)O)ccc54)ccc23)CC1 ; [Cl-]]

Conjugates of Reactive Compounds

In one embodiment, the compound (quenching compound or precursor compound) is substituted by at least one group -L-$R_x$, where $R_x$ is the reactive group that is attached to the compound by a covalent linkage L, as described in detail above for the dyes. The compounds with a reactive group ($R_x$) label a wide variety of organic or inorganic substances that contain or are modified to contain functional groups with suitable reactivity, resulting in chemical attachment of the conjugated substance ($S_e$), represented by -L-$S_c$.

In one embodiment, the conjugated substance (Se) is a natural or synthetic nucleic acid base, nucleoside, nucleotide or a nucleic acid polymer, including those that are protected, or modified to possess an additional linker or spacer for attachment of the compounds, such as an alkynyl linkage, an aminoallyl linkage, or other linkage. In some embodiments, the conjugated nucleotide is a nucleoside triphosphate or a deoxynucleoside triphosphate or a dideoxynucleoside triphosphate.

Although it is generally preferably to incorporate a dye onto a nucleic acid using an automated DNA synthesizer, dyes not available in amidite form or unable to survive harsh cleavage/deprotection (C/D) conditions are routinely introduced post-synthetically to amine-functionalized oligonucleotides via their NHS ester derivatives. However, such labeling reactions usually require a dye-NHS ester in large excess, for example, 10 to 20-fold in molar equivalency, over the nucleic acid counterpart, due to competing side reactions, including hydrolysis and amino-lysis of residual amine impurities from synthesis.

In view of this, the present inventors have developed an alternative strategy using azido-derivatized dye to label a nucleic acid, such as an oligonucleotide, having a strained cyclooctyne moiety, via a highly efficient, Cu-free click reaction. Due to the specific nature of triazole formation between azide and cyclooctyne functional groups, very few side reactions compete or interfere with such reactions. As an example, an azido-derivative of a cyanine dye was reacted with a cyclooctyne containing oligonucleotide during the post-C/D concentrating step to take advantage of faster kinetics of the click reaction under high concentration of azide and octyne moieties. Consequently, near-quantitative conversion of a cyclooctyne containing oligonucleotide to an azido-derivatized dye was achieved using only 20% molar excess (or 1.2 equivalent) of the dye over oligonucleotide.

This alternative labeling scheme based on a Cu-free, azide/cyclooctyne click chemistry to produce dye-oligonucleotide conjugates had the following advantages over the commonly employed NHS ester/amine chemistry: 1. Lower molar equivalency of azido-dye needed for conjugation than its NHS ester counterpart, which translates into reduced reagent costs; 2. Due to their chemical inertness, azido-dyes can be reconstituted and stored in ready-to-use solution form much longer than their NHS ester counterpart (or a longer shelf-life); and 3. The post-labeling clean-up workflow can be further streamlined to reduce labor costs.

Azides and alkynes can undergo Cu-free, i.e., catalyst free, [3+2] cycloaddition by using the reaction of activated alkynes with azides. Such catalyst-free [3+2] cycloaddition can be used in methods described herein to conjugate a dye to a biomolecule, such as an oligonucleotide. Alkynes can be activated by ring strain such as, by way of example only, eight-membered ring structures, or nine-membered, appending electron-withdrawing groups to such alkyne rings, or alkynes can be activated by the addition of a Lewis acid such as, by way of example only, Au(I) or Au(III). Alkynes activated by ring strain have been described, and has been referred to as "copperless" or Cu-free [3+2] cycloaddition. For example, the cyclooctynes and difluorocyclooctynes described by Agard et al., J. Am. Chem. Soc, 126 (46): 15046-15047 (2004), the dibenzocyclooctynes described by Boon et al., PCT International Publication No. WO 2009/067663 A1 (2009), the aza-dibenzocyclooctynes described by Debets et al., Chem. Comm., 46:97-99 (2010), and the cyclononynes described by Dommerholt et al., Angew. Chem. 122:9612-9615 (2010)). Additional descriptions of Cu-free reaction of activated alkynes with azides can be found in PCT/US2006/042287, PCT/IB2007/003472, and PCT/US2013/066765. In certain embodiments of the methods described herein, the dye can possess an azide moiety, whereupon the biomolecule possesses an activated alkyne moiety; while in other embodiments the dye can possess an activated alkyne moiety, and the biomolecule possesses an azide moiety. In various embodiments, the cyclooctyne is selected from cyclooctyne (OCT), monofluorinated cyclooctyne (MOFO), difluorocyclooctyne (DIFO), dimethoxyazacyclooctyne (DIMAC), dibenzocyclooctyne (DIBO), dibenzoazacyclooctyne (DIBAC), biarylazacyclooctynone (BARAC), bicyclononyne (BCN), 2,3,6,7-tetramethoxy-DIBO (TMDIBO), sulfonylated DIBO (S-DIBO), carboxymethylmonobenzocyclooctyne (COMBO), and pyrrolocyclooctyne (PYRROC).

Exemplary nucleic acid polymer conjugates are labeled, single-, double-, or multi-stranded, natural or synthetic DNA or RNA, DNA or RNA oligonucleotides, or DNA/RNA hybrids, or incorporate an unusual linker such as morpholine derivatized phosphates or peptide nucleic acids such as N-(2-aminoethyl)glycine units. When the nucleic acid is a synthetic oligonucleotide, it typically contains fewer than 50 nucleotides, more typically fewer than 25 nucleotides. Larger nucleic acid polymers are typically prepared from labeled nucleotides or oligonucleotides using oligonucleotide-primed DNA polymerization, such as by using the polymerase chain reaction or through primer extension, or by terminal-transferase catalyzed addition of a labeled nucleotide to a 3'-end of a nucleic acid polymer. Typically, the compound is attached via one or more purine or pyrimidine bases through an amide, ester, ether or thioether bond; or is attached to the phosphate or carbohydrate by a bond that is an ester, thioester, amide, ether or thioether. Alternatively, the compound is bound to the nucleic acid polymer by chemical post-modification, such as with platinum reagents, or using a photoactivatable molecule such as a conjugated psoralen. In one embodiment, the quenching moiety is attached to the nucleotide, oligonucleotide or nucleic acid polymer via a phosphoramidite reactive group, resulting in a phosphodiester linkage.

The quenching compounds can accept energy from a wide variety of fluorophores, provided that the quenching compound and the fluorophore are in sufficiently close proximity for quenching to occur, and that at least some spectral overlap occurs between the emission wavelengths of the fluorophore and the absorption band of the quenching compound. This overlap may occur with emission of the donor occurring at a lower or even higher wavelength emission maximum than the maximal absorbance wavelength of the quenching compound, provided that sufficient spectral overlap exists. In some embodiments, the quenching compound is only dimly fluorescent, or essentially nonfluorescent, so that energy transfer results in little or no fluorescence emission. In one aspect, the quenching compound is essentially nonfluorescent and has a fluorescence quantum yield of less than about 0.05. In another aspect, the quenching compound has a fluorescence quantum yield of less than about 0.01. In yet another aspect, the quenching compound has a fluorescence quantum yield of less than about 0.005.

Typically, quenching occurs through FRET between a donor and a quenching acceptor. The degree of FRET exhibited by a donor acceptor pair can be represented by the Forster equation:

$$R_o = (8.8 \times 10^{23} \cdot \kappa^2 \cdot n^{-4} \cdot QY_D \cdot J(\lambda))^{1/6} \text{Å}$$

wherein the Förster radius ($R_o$) represents the separation distance at which the energy transfer between a donor and acceptor is 50% efficient (i.e. 50% of excited donors are deactivated by FRET);
$\kappa^2$=dipole orientation factor (range 0-4, $\kappa^2$=⅔ for randomly oriented donors and acceptors);
$QY_D$=fluorescence quantum yield of the donor in the absence of the acceptor;
n=refractive index; and
$J(\lambda)$=spectral overlap integral.

Because the degree of energy transfer is dependent on the spectral overlap integral, it can be readily appreciated that the spectral properties of the donor and acceptor dyes have a strong effect on the energy transfer observed, as shown in the following equation:

$$J(\lambda) = \int \varepsilon_A(\lambda) \cdot F_D(\lambda) \cdot \lambda^4 d\lambda \, \text{cm}^3 \, \text{M}^{-1}$$

wherein $\varepsilon_A(\lambda)$ is the absorption spectrum of the acceptor expressed in terms of molar extinction coefficient $\varepsilon_A$. $F_D(\lambda)$ is the fluorescence emission spectrum of the donor, with the fluorescence intensity ($F_D$) expressed as a fraction of the total integrated intensity.

It should be readily appreciated that the degree of energy transfer during FRET, and therefore quenching, is highly dependent upon the separation distance between the fluorophore and the quenching compound. In molecular systems, a change in fluorescence quenching typically correlates well with a change in the separation distance between the fluorophore molecule and the quenching compound molecule. Any fluorophore with sufficient spectral overlap with a quenching compound is a suitable donor for the applications. The greater the degree of overlap, the greater the overall quenching observed.

In one embodiment, the disassembly, cleavage or other degradation of a molecular structure comprising the described fluorophore and quencher is detected by observing the partial or complete restoration of fluorescence of a fluorophore. In some embodiments, the initially quenched fluorescence of a fluorophore associated with the structure becomes dequenched upon being removed from the close proximity to a quenching compound by the disassembly, cleavage, or degradation of the molecular structure. The quenching compound is optionally associated with the same molecular structure as the fluorophore, or the donor and acceptor are associated with adjacent but distinct subunits of the structure. The following systems, among others, can be analyzed using the described energy transfer pairs to detect and/or quantify structural disassembly: detection of protease activity using fluorogenic substrates (for example HIV protease assays); detection of enzyme-mediated protein modification (e.g. cleavage of carbohydrates/fatty acids, phosphates, prosthetic groups); immunoassays (via displacement/competitive assays); detection of DNA duplex unwinding (e.g. helicase/topoisomerase/gyrase assays); nucleic acid strand displacement; ds DNA melting; nuclease activity; lipid distribution and transport; and TaqMan assays.

Structure disassembly is typically detected by observing a partial or complete restoration of fluorescence, as a conjugated substance is exposed to a degradation conditions of interest for a period of time sufficient for degradation to occur. A restoration of fluorescence indicates an increase in separation distance between the fluorophore and quenching compound, and therefore a degradation of the conjugated substance.

Probe

Various manufacturers provide instruments capable of detecting multiplex PCR assays. As one example, Thermo Fisher Scientific (Waltham, Mass.) provides 4-plex TaqMan assays for real time detection of nucleic acids targets on Thermo Fisher Scientific instruments, such as, Vii7, Quant Studio, etc. Most of these real time qPCR instruments have the optical capability to run 6-plex TaqMan assay. In some embodiments, the TaqMan multiplex probes have FAM, VIC, ABY and JUN reporter dyes and QSY7 quencher. QSY7 quencher cannot efficiently quench reporter dyes with fluorescence maxima >630 nm. Thus, in one embodiment, the ideal dye for detection in PCR implementing 5th and 6th filters has emission maxima at 665 nm and 700 nm respectively. In one embodiment, the 5th and 6th reporter dyes should be available as a phosphoramidite derivative, which makes it easier to synthesize TaqMan probes in high quality and in reduced cost. In one embodiment, the described probe(s) are included in a multiplex PCR assay as the 5th and/or 6th probe, the assay also comprising probes comprising the following dye/quencher combinations: JUN/QSY, VIC/QSY, FAM/MGBNFQ, and ABY/QSY. The dyes of these probes have a maximal emission of: FAM ~517 nm, VIC ~551 nm, ABY ~580 nm, and JUN ~615 nm. In various embodiments, the described probes also include a minor groove binder (MGB) moiety at the 3' end that increases the melting temperature ($T_m$) of the probe and stabilizes probe-target hybrids. In some embodiments, the use of a MGB allows the probe to be shorter than traditional probes, which can provide better sequence discrimination and flexibility to accommodate more targets.

In addition, the present inventors have discovered that benzyl substitution of the indole of a cyanine dye gave an unexpectedly large red shift in the cyanine dye's emission maximum. For example, the following benzyl substituted dye was shifted by 8 nm to the red in comparison to a dye without the benzyl derivative, with an emission shift from 697 nm to 705 nm.

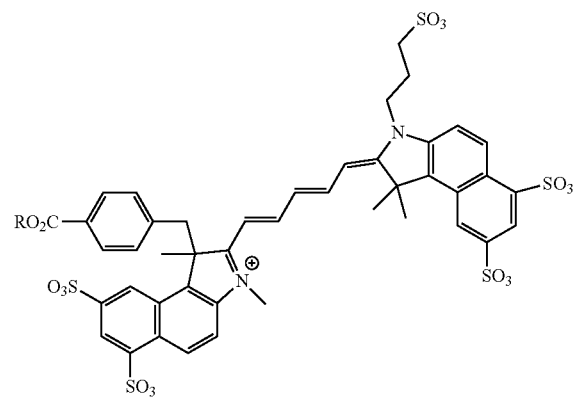

This red shift in emission wavelength makes the benzyl dye significantly easier to resolve from other dyes emitting at similar emission wavelengths. Because there is reduced spectral overlap, when used in multiplex (e.g., 6-plex) qPCR applications, the benzyl derivative cyanine can result in reduced cross talk between dyes emitting at neighboring wavelengths and minimize noise associated with their signal deconvolution. Minimizing noise can also facilitate greater detection sensitivity by allowing for use of a larger detection window. In various embodiments, this described benzyl-substituted dye is incorporated into the described probe, and allows for multiplex qPCR methods, including 6-plex qPCR.

In one embodiment, the described probe comprises one of the fluorophore/reporter dyes described above and one of the quenchers described above, where the fluorophore and the quencher are each covalently conjugated to an oligonucleotide. Examples of probes suitable for multiplex PCR applications can include a carbocyanine reporter dye, as described herein, that emits in the red spectral region upon excitation at an appropriate wavelength. Representative examples of carbocyanine dyes emitting in the red spectral region include e.g., Alexa Fluor 647, Alexa Fluor 676, DyLight 647, or DyLight 677, available from Thermo Fisher Scientific (Waltham, Mass.) and derivatives thereof. In one embodiment, the fluorophore and the quencher are covalently attached to the termini of an oligonucleotide. A representative example of a fully assembled probe is as follows:

combines reverse transcription of RNA into DNA, referred to as complementary DNA or cDNA, and amplification of specific cDNA targets using polymerase chain reaction (PCR). In various embodiments, the combination of RT-PCR and qPCR are routinely used for nucleic acid analysis, such as determining gene expression and quantification of viral RNA in research and clinical settings. However, RT-PCR can be used without qPCR, for example, to enable molecular cloning, sequencing or simple detection of RNA and qPCR may be used without RT-PCR, for example, to quantify the copy number of a specific piece of DNA.

In particular, a method for amplifying and detecting multiple target DNA sequences comprising providing a composition or reaction mixture comprising the described probe, subjecting the reaction mixture to a thermocyling protocol such that amplification of said multiple target sequences can take place, and monitoring amplification by detecting the fluorescence of the described probe at least once during a plurality of amplification cycles. In one embodiment, the method comprises a 5-plex or 6-plex multiplex PCR assay where the described probes allow for detection of the 5th and/or 6th nucleic acid target.

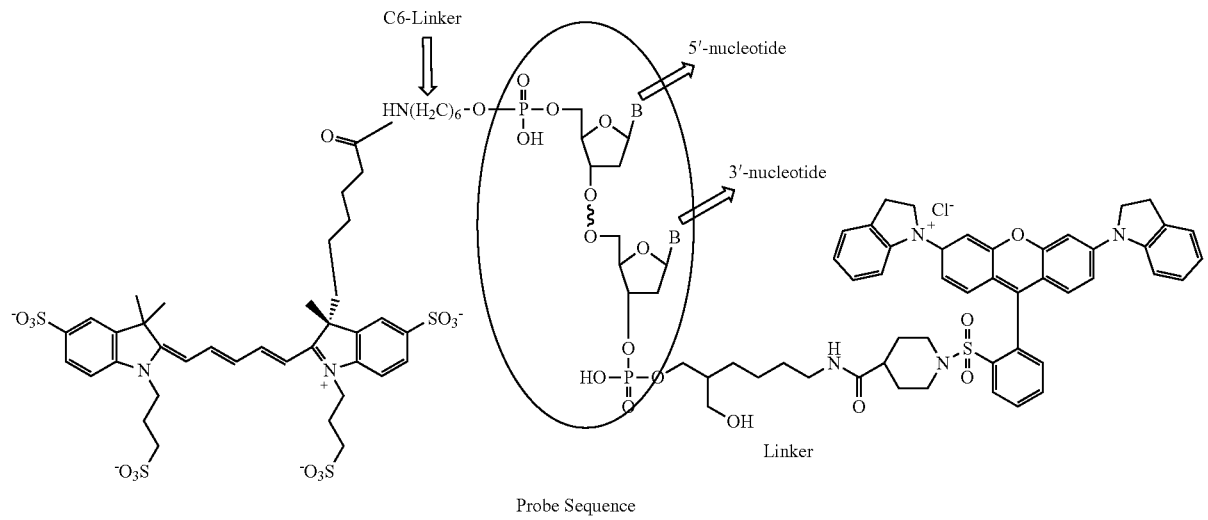

The described probe can be synthesized according to methods known in the art. For example, in one embodiment, the fluorophore and the quencher are covalently conjugated to the termini of an oligonucleotide using the conjugation chemistries and reactive groups described above. In another example, the quencher or probe may be conjugated to a solid support and the oligonucleotide is synthesized from the attached quencher or probe using standard oligonucleotide synthesis methods, such as a DNA synthesizer, and then the other of the quencher or probe is covalently attached to the terminus of the synthesized oligonucleotide. An exemplary embodiment of attaching the quencher to a solid support is provided in the Example.

Methods and Kits

In a further aspect, methods and kits for performing singleplex or multiplex PCR, such as qPCR, end-point PCR, or RT-PCR, using the described probe are provided. End point PCR is the analysis after all cycles of PCR are completed. Unlike qPCR, which allows quantification as template is doubling (exponential phase), end point analysis is based on the plateau phase of amplification. RT-PCR The detection of the signal may be accomplished using any reagents or instruments that detect a change in fluorescence from a fluorophore. For example, detection may be performed using any spectrophotometric thermal cycler. Examples of spectrophotometric thermal cyclers include, but are not limited to, Applied Biosystems (AB) PRISM® 7000, AB 7300 real-time PCR system, AB 7500 real-time PCR system, AB PRISM® 7900HT, Bio-Rad ICycler IQ™, Cepheid SmartCycler® II, Corbett Research Rotor-Gene 3000, Idaho Technologies R.A.P.I.D.™, MJ Research Chromo 4™, Roche Applied Science LightCycler®, Roche Applied Science LightCycler®2.0, Stratagene Mx3000P™, and Stratagene Mx4000™. It should be noted that new instruments are being developed at a rapid rate and any like instruments may be used for the methods. In one embodiment, and as an example of a 6-plex multiplex assay, the following filter sets may be used: 1st 520±15, 2nd 558±12, 3rd 587±10, 4th 623±14, 5th 682±14, and 6th 711±12. This filter set is standard for Vii7, Quant Studio 5 and Quant Studio 7 real-time instruments.

The nucleic acid target(s) of the described method may be any nucleic acid target known to the skilled artisan. Further, the targets may be regions of low mutation or regions of high mutation. For example, one particularly valuable use of the methods disclosed herein involves targeting highly mutated nucleic acids, such as RNA viral genes, or regions of high genetic variability, such a single nucleotide polymorphisms (SNPs). In some embodiments, the targets may be fragmented or degraded, such as material from forensic samples and/or fixed tissues. The targets may be any size amenable to amplification. One particularly valuable use of the methods and compositions provided herein involves the identification of short fragments, such as siRNA and miRNA. Another particularly valuable use is for samples that may have fragmented and/or degraded nucleic acid, such as fixed samples or samples that have been exposed to the environment. Thus, the methods may be used for biopsy tissue and forensic DNA for example. The targets may be purified or unpurified. The targets may be produced in vitro (for example, a cDNA target) or can be found in biological samples (for example, an RNA or a genomic DNA (gDNA) target). The biological sample may be used without treatment or the biological samples may be treated to remove substances that may interfere with the methods disclosed herein.

The probes provided herein may be used in methods of diagnosis, e.g., SNP detection, identification of specific biomarkers, etc., whereby the probes are complementary to a sequence (e.g., genomic) of an infectious disease agent, e.g., of human disease including but not limited to viruses, bacteria, parasites, and fungi, thereby diagnosing the presence of the infectious agent in a sample having nucleic acid from a patient. The target nucleic acid may be genomic or cDNA or mRNA or synthetic, human or animal, or of a microorganisms, etc. In other embodiments, the probes may be used to diagnose or prognose a disease or disorder that is not caused by an infectious agent. For example, the probes may be used to diagnose or prognose cancer, autoimmune diseases, mental illness, genetic disorders, etc. by identifying the presence of a mutation, polymorphism, or allele in a sample from a human or animal. In some embodiments, the probe comprises the mutation or polymorphism. Additionally, the probes may be used to evaluate or track progression of treatment for a disease or disorder.

Also provided are compositions, such as a reaction mixture or master mix, comprising the described probe. In one embodiment, the composition for PCR, such as for real-time or quantitative PCR, end-point PCR, or RT-PCR, comprises at least one of the described probes. In one embodiment, the composition or reaction mixture or master mix for PCR (e.g., qPCR, end-point PCR, or RT-PCR) comprises probes for allowing for detection of 4 target nucleic acids and the described probe(s) allowing for detection of at least one of a 5th and/or a 6th target nucleic acid, each of the described probes consisting of a FRET donor moiety, i.e., fluorophore, and a FRET acceptor moiety, i.e., quencher, where the fluorophore has an emission maximum between about 650 and 720 nm. The absorbance maximum of the quencher as described herein is between 660-668 nm. The absorbance range of the quencher as described herein is 530-730 nm. In an alternate embodiment, labeling reagents are provided for conjugating the described fluorophore and quencher to an oligonucleotide of choice.

In addition, such a composition or reaction mixture or master mix may comprise one or several compounds and reagents selected from the following list: Buffer, applicable for a polymerase chain reaction, deoxynucleoside triphosphates (dNTPs), DNA polymerase having 5' to 3' exonuclease activity, at least one pair or several pairs of amplification primers and/or additional probes.

In yet another aspect, a kit comprising at least one of the described probe(s) is provided. In addition, a kit may comprise one or several other compounds and reagents selected from the following list: Buffer, applicable for a polymerase chain reaction, deoxynucleoside triphosphates (dNTPs), DNA polymerase having 5' to 3' exonuclease activity, at least one or multiple pairs of amplification primers. The kit may also comprise an internal control DNA or standard. Regarding RT-PCR, the kit may further include a reverse transcriptase. Each of the components disclosed above may be stored in a single storage vessel and packaged separately or together. Yet, any combination of components for storage within the same vessel is possible as well.

Examples

The quencher compound may be attached to a solid support, e.g., a bead, to provide a substrate for construction of a probe using an oligonucleotide synthesizer, in accordance with the following reaction scheme:

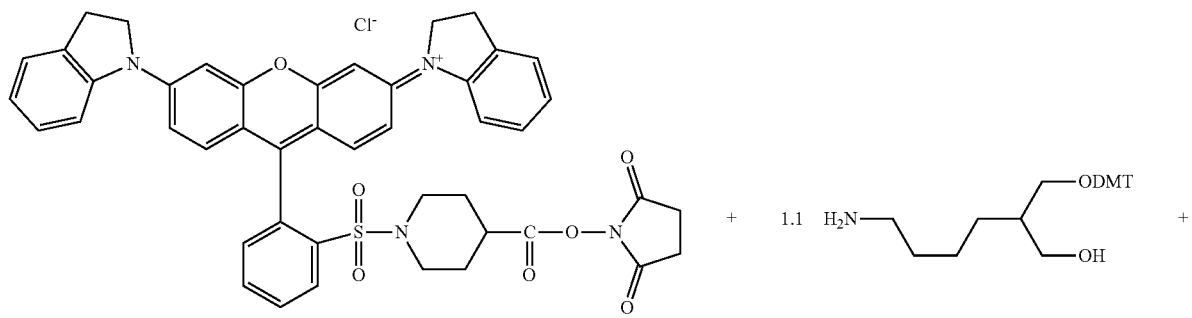

1

-continued
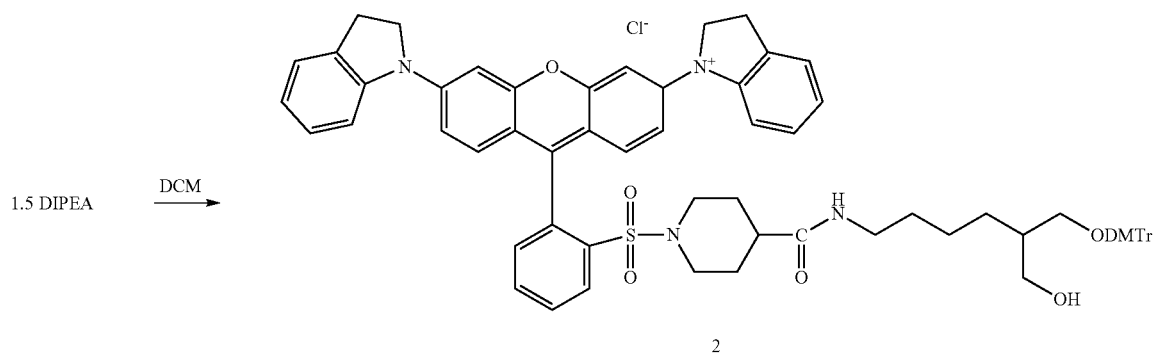
1.5 DIPEA, DCM
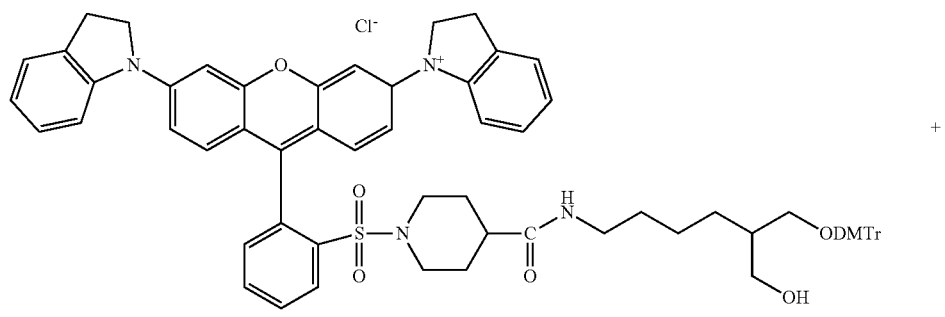
+
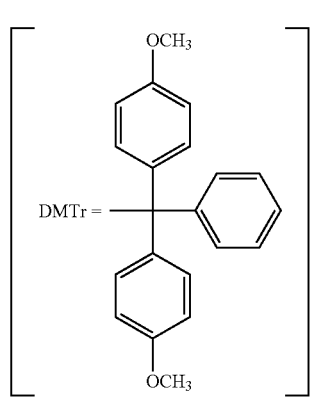
DMTr =
2.5 DIPEA, DCM -continued
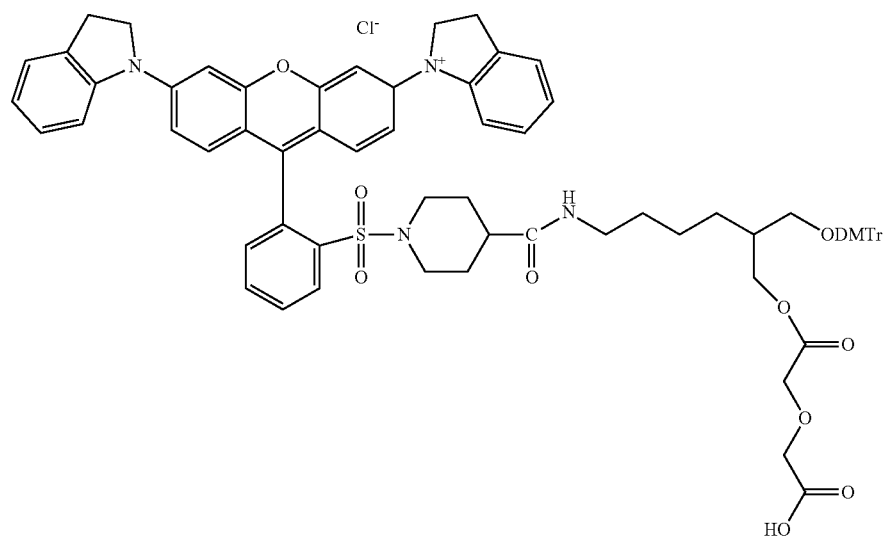
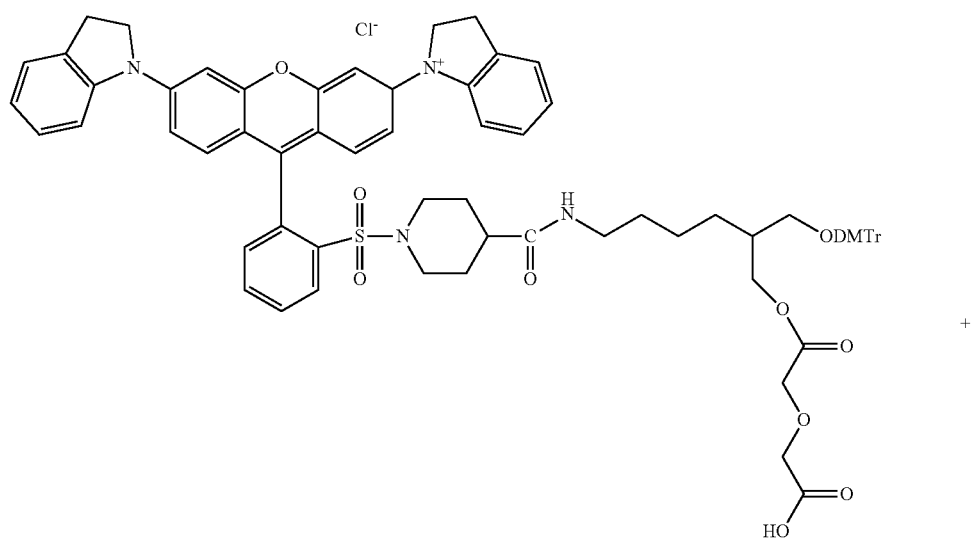
+
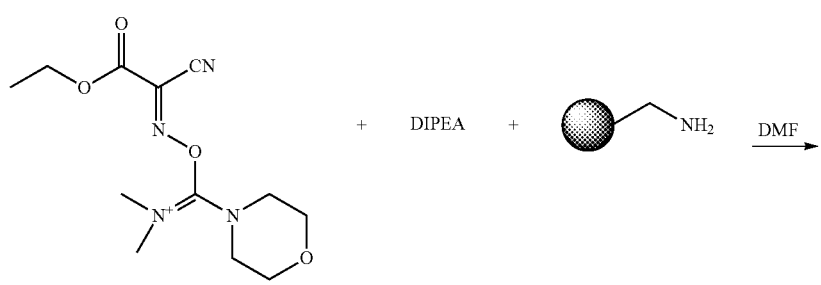

-continued

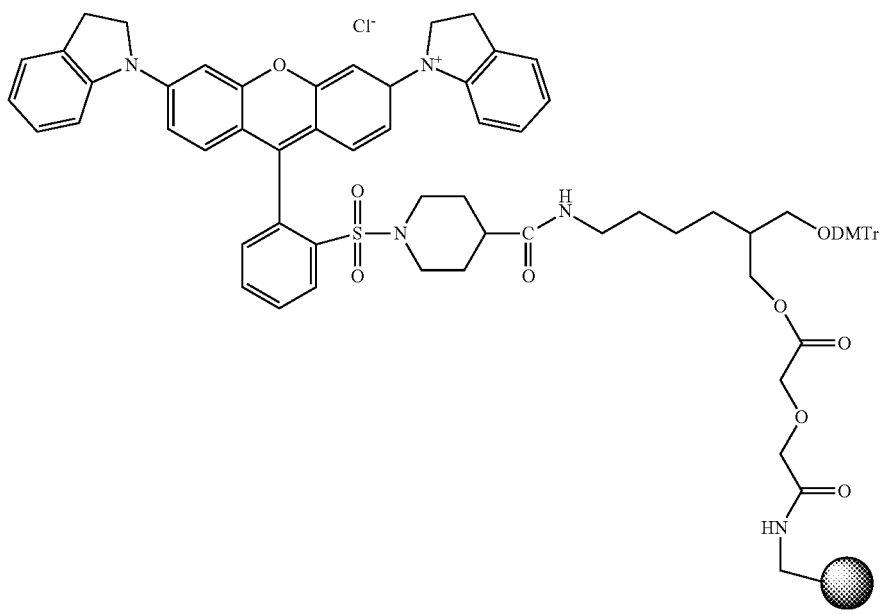

4

The following exemplary synthetic procedure may be easily generalized to any of the quenchers described above. Thus, the above reaction scheme and below procedure are not meant to limit the scope of the claimed subject matter.

In one embodiment, a representative derivatized quencher (2) can be synthesized according to the following procedure.

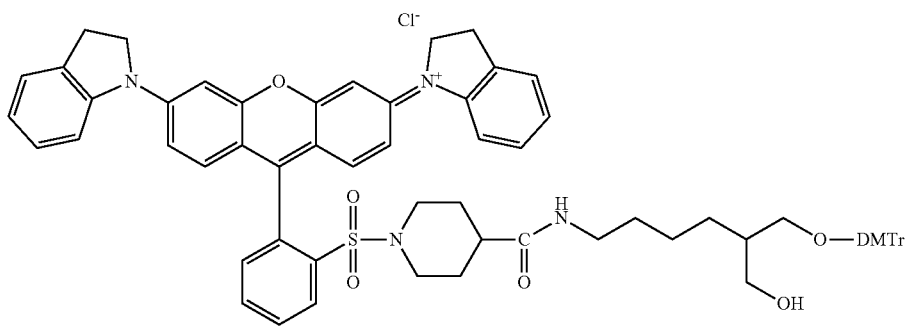

Representative quencher (1) NHS ester (100 mg, 0.123 mmol) was dissolved in 1 mL of anhydrous DCM. 1-O-DMT-2-(4-Aminobutyl)-1,3-propanediol (61 mg, 0.14 mmol) dissolved in 1213 μL of DCM (a 5% solution) was mixed with Diisopropylethylamine (32 μL, 0.19 mmol). This was added dropwise to representative quencher (1) NHS ester at room temperature and stirred for 30 min under nitrogen. The crude representative quencher (2) in DCM solution was diluted with DCM (50 mL) and washed with 1% citric acid, water, and then brine. The organic layer was dried over $Na_2SO_4$ and evaporated to dryness. Further high vacuum drying overnight provided 125 mg (88% yield) of quencher (2) as a dark blue solid. The product was used in the next step without further purification. NMR (400 MHz, $CD_2Cl_2$): δ 8.14 (1H, d), 7.83 (2H, m), 7.60 (2H, d), 7.50-7.10 (22H, m), 6.80 (4H, m) 4.40 (2H, m), 4.25 (2H, m), 3.75 (6H, s), 3.62-3.50 (4H, m), 3.30 (6H, m), 3.05 (2H, m), 2.51 (2H, t), 2.40 (1H, t), 1.72 (2H, d), 1.50-1.20 (7H, m). LC/HRMS (ESI+) Calcd for [M+] 1113.48; found 1113.47. Elutions were done with a 20 minute linear gradient from 40 to 100% acetonitrile (against 0.1 M triethylammonium acetate). 1.0 ml/min flow rate. Detection at 285 nm and 655 nm.

In another embodiment, a representative quencher including a diglycolic linker (3) can be synthesized according to the following procedure.

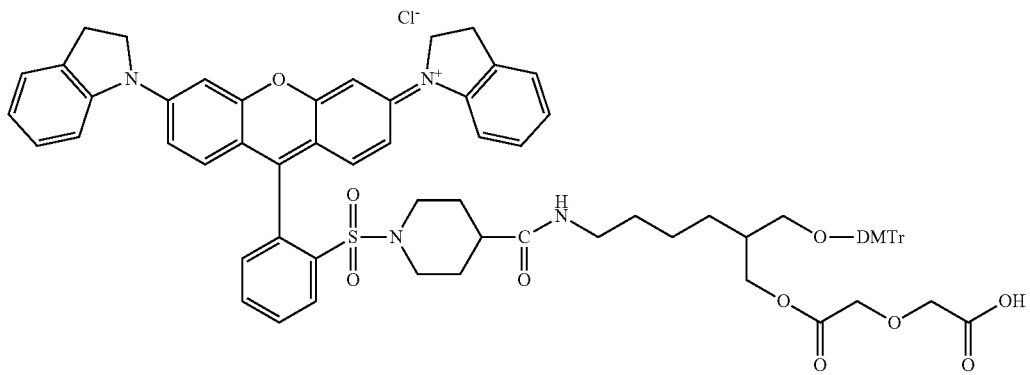

Representative quencher (2) (125 mg, 0.109 mmol) was dissolved in 3 mL of anhydrous DCM. DIPEA (47 μL, 0.27 mmol) was added, followed by diglycolic anhydride (25 mg, Representative quencher (4) can be linked to a solid support, e.g., polystyrene bead, according to the following procedure.

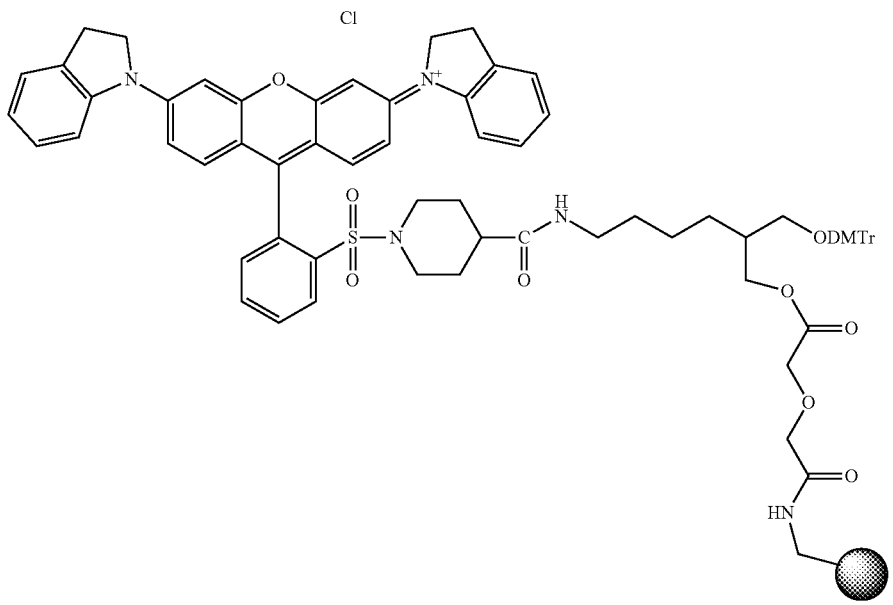

0.22 mmol). The solution was stirred for 30 min under nitrogen. The reaction solution was concentrated and the residue re-dissolved in 1% TEA/DCM and purified on silica gel column chromatography (pre-equilibrated in 10%-1% TEA/DCM) using 5-15% MeOH/DCM/1% TEA eluent. The purified pool was concentrated and then washed with 1% citric acid, water, and brine. The organic layer was dried over anhydrous $Na_2SO_4$, evaporated to dryness, and then further dried under high vacuum to yield representative quencher diglycolic linker (3) (96 mg, 69% yield) as a dark blue solid. $^1$H NMR (400 MHz, $CD_2Cl_2$): δ 8.14 (1H, d), 7.85 (2H, m), 7.60 (2H, d), 7.52-7.10 (22H, m), 6.79 (4H, d), 4.35 (2H, m), 4.25 (2H, m) 4.05 (3H, s/m), 3.80 (2H, s), 3.72 (6H, s), 3.28 (6H, m), 3.00 (2H, m), 2.90 (2H, m), 2.50 (2H, t), 2.32 (1H, t), 1.65 (2H, m), 1.50-1.10 (7H, m). LC/HRMS ($ESI^+$) Calcd for $[M^+]$ 1229.49; found 1229.49. Elutions were done with a 20 minute linear gradient from 40 to 100% acetonitrile (against 0.1 M triethylammonium acetate). 1.0 ml/min flow rate. Detection at 285 nm and 655 nm.

Representative quencher diglycolic linker (3) (357 mg, 0.20 mmol) was dissolved in 50 mL of anhydrous DMF. To this was added aminomethyl polystyrene (6.77 g, 0.223 mmol, 33 umol/g amine), DIPEA (194 uL, 1.12 mol), and COMU or 1-Cyano-2-ethoxy-2-oxoethylidenaminooxy)dimethyl-amino-morpholino-carbenium hexafluorophosphate (287 mg, 0.669 mmol). The mixture was shaken for 3 hr. The solvent was removed and the resin was washed 3 times each with 50 mL of DMF, MeCN, and DCM. Any remaining amine groups on the resin were then capped by reacting with 50 mL acetic anhydride/pyridine in THF mixed with 50 mL of 1-N-methylimidazole in THF and shaken for 1 hr. The solvent was removed and the resin washed 3 times each with THF, MeCN, and DCM. The resin was then dried overnight under high vacuum to yield 6.60 g of light blue powder representative quencher (4). The resin support was tested for any residual amine groups using the ninhydrin test and found to be 0.94 umol/g amine (negligible). The amount of representative quencher coupled to the support was determined by cleaving off the DMT group of a weighed aliquot of the representative quencher PS sample with a known volume of 0.1M toluenesulfonic acid in MeCN. The absorbance at 498 was obtained and using the extinction coefficient (76,500$M^{-1}$ $cm^{-1}$), mass, and volume, the loading of representative quencher per g of polystyrene was found to be 22 μmol/g. The typical range found for this coupling condition was 20-27 μmol/g.

As an example, a benzyl-substituted cyanine dye with an emission shift from 697 nm to 705 nm from the non-benzyl substituted cyanine dye, as described, can be synthesized as follows using synthetic techniques that are well-established in the art.

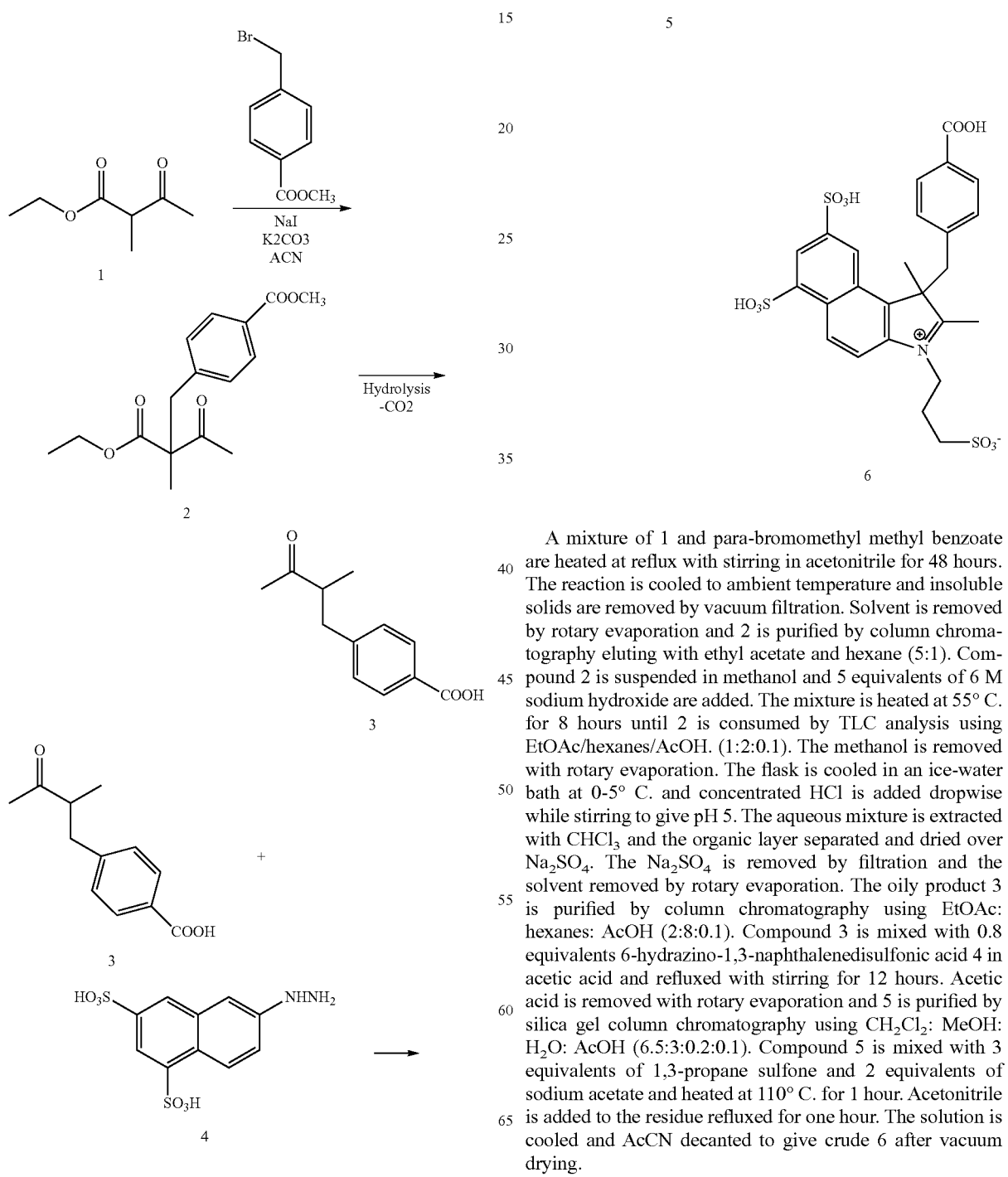

A mixture of 1 and para-bromomethyl methyl benzoate are heated at reflux with stirring in acetonitrile for 48 hours. The reaction is cooled to ambient temperature and insoluble solids are removed by vacuum filtration. Solvent is removed by rotary evaporation and 2 is purified by column chromatography eluting with ethyl acetate and hexane (5:1). Compound 2 is suspended in methanol and 5 equivalents of 6 M sodium hydroxide are added. The mixture is heated at 55° C. for 8 hours until 2 is consumed by TLC analysis using EtOAc/hexanes/AcOH. (1:2:0.1). The methanol is removed with rotary evaporation. The flask is cooled in an ice-water bath at 0-5° C. and concentrated HCl is added dropwise while stirring to give pH 5. The aqueous mixture is extracted with $CHCl_3$ and the organic layer separated and dried over $Na_2SO_4$. The $Na_2SO_4$ is removed by filtration and the solvent removed by rotary evaporation. The oily product 3 is purified by column chromatography using EtOAc: hexanes: AcOH (2:8:0.1). Compound 3 is mixed with 0.8 equivalents 6-hydrazino-1,3-naphthalenedisulfonic acid 4 in acetic acid and refluxed with stirring for 12 hours. Acetic acid is removed with rotary evaporation and 5 is purified by silica gel column chromatography using $CH_2Cl_2$: MeOH: $H_2O$: AcOH (6.5:3:0.2:0.1). Compound 5 is mixed with 3 equivalents of 1,3-propane sulfone and 2 equivalents of sodium acetate and heated at 110° C. for 1 hour. Acetonitrile is added to the residue refluxed for one hour. The solution is cooled and AcCN decanted to give crude 6 after vacuum drying.

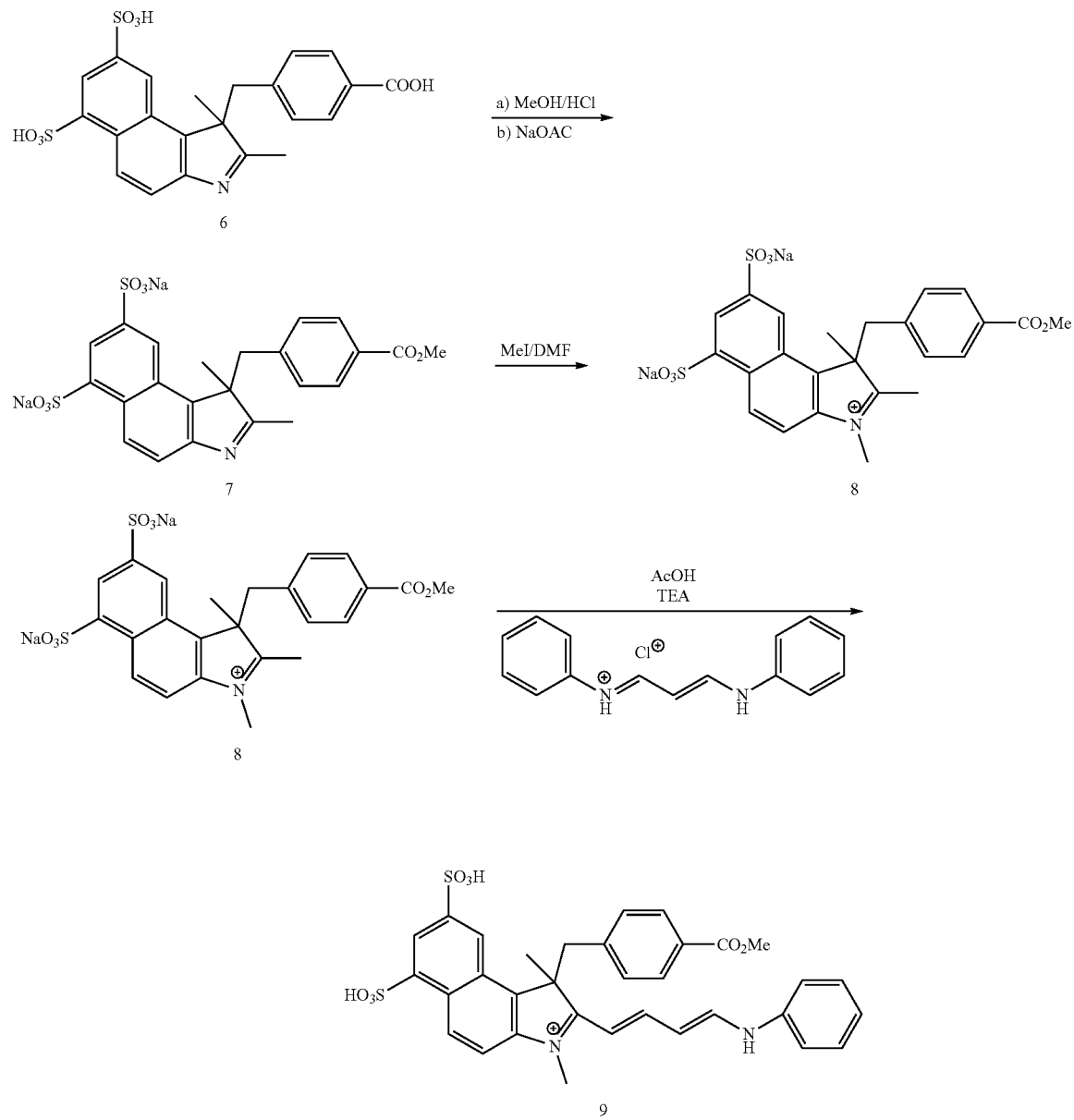
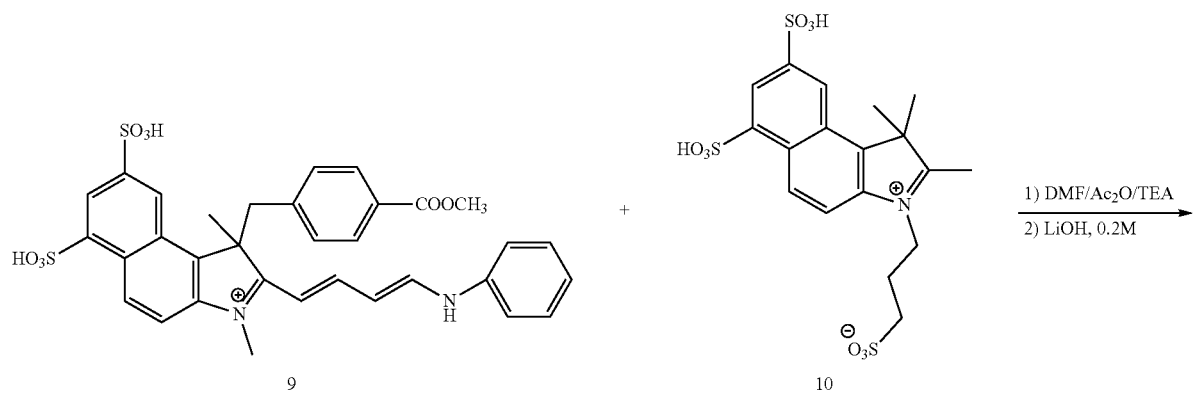

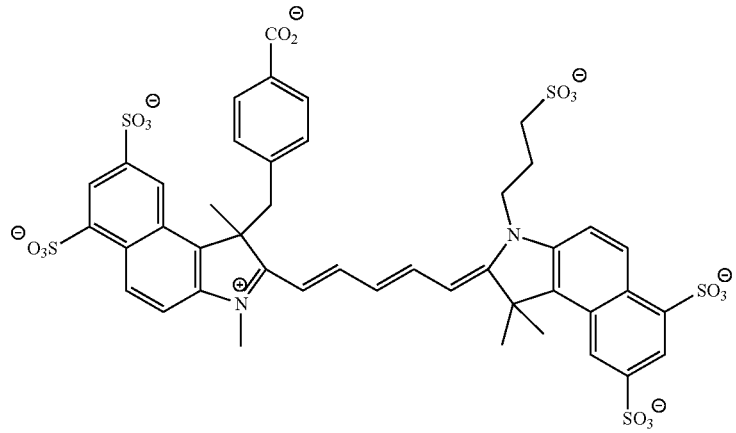

11

Compound 6 is suspended in methanolic HCl 0.5 N and refluxed with stirring for 1 hour. The Solvent is removed by rotary evaporation. The residue is suspended in Methanol and 1.1 equivalents of sodium acetate is added withy stirring for 10 minutes. The methanol is removed by rotary evaporation and the residue dried under vacuum. The residue is suspended in DMF with 0.1% diisopropyl ethyl amine and 5 equivalents of methyl iodide and heated with stirring for 8 hours. Compound 8 is purified by column chromatography eluting with $CH_2Cl_2$: MeOH: AcOH (80:20:1). Compound 8 and 1 equivalent of malonaldehyde bis(phenylimine) monohydrochloride are suspended in acetic acid and 0.1 equivalent of triethylamine is added. The mixture is heated at 110° C. for 1 hour. The reaction is cooled and EtOH (~2×AcOH volume) is added and crude 9 precipitated with diethyl ether and collected by filtration. Compound 9 is purified by column chromatography eluting with $CH_2Cl_2$: MeOH: AcOH (80:20:1). Compound 10 (20 mg) is suspended in DMF (2 mL). 1 equivalent of Compound 9 is added with stirring. Acetic anhydride is added (3.5 equivalents) and then triethylamine (6.4 equivalents) is added with stirring and the reaction stirred at room temperature for two hours. The solution is concentrated by with rotary evaporation. EtOAc is added to the concentrate and stirred for 4-12 hours. The blue-green solid is collected by suction filtration. The solid is suspended in 0.2 M LiOH in water (15 mg/1 ml), stir rt 3 hrs. Add Dowex H+ resin 50W-X8, H+, 20-50 mesh (0.5 gram resin/1 ml LiOH) Stir 15 minutes until neutral, filter off dye solution. Dye 11 is purified by column chromatography eluting with $CH_2Cl_2$: MeOH: AcOH (80:20:1).

It is to be understood that, while the foregoing embodiments have been described in detail by way of illustration and example, numerous modifications, substitutions, and alterations are possible without departing from the spirit and scope of the claimed subject matter. Each of the references cited herein is incorporated by reference in its entirety.

Further aspects of the present disclosure as set forth in the following numbered clauses:

Clause 1. A probe comprising a product of conjugation of:

a) a dye having a general Formula Ia, Formula Ib, Formula Ic, or Formula Id

Formula Ia

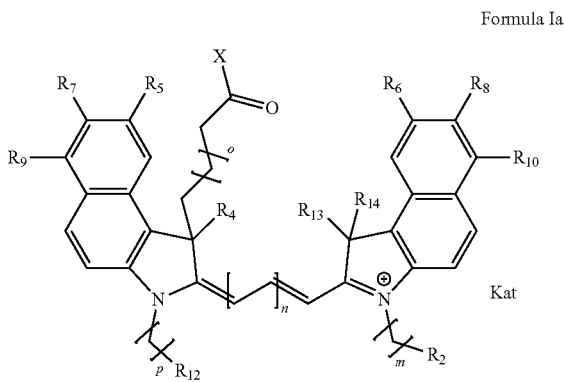

Formula Ib

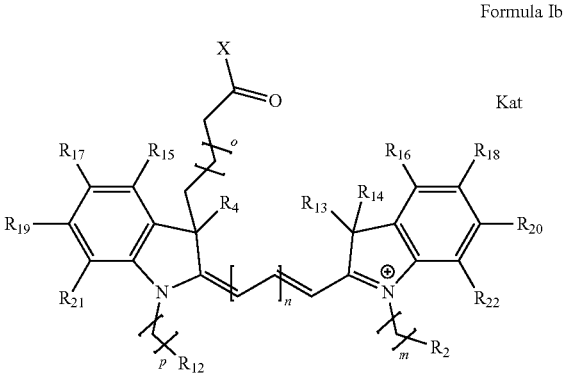

-continued

Formula Ic

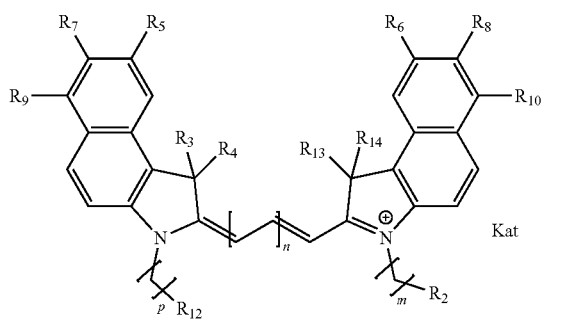

Formula Id

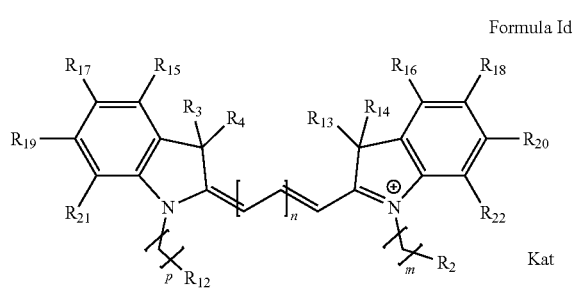

wherein each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;

each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;

each of $R_2$ and $R_{12}$ is the same or different and is selected from the group consisting of H and $SO_3$;

X is selected from the group consisting of —OH, —SH, —$NH_2$, —NH—$NH_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-CO—NHS, —NR-L-CO-STP, —NR-L-CO-TFP, —NR-L-CO-benzotriazole, —NR-L-CHO, —NR-L-maleimide, —$NH(CH_2CH_2O)_zCH_2CH_2N_3$, —NR-L-NH—CO—$CH_2$—I, and an azide ($N_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive;

b) a quencher having general Formula II

Formula II

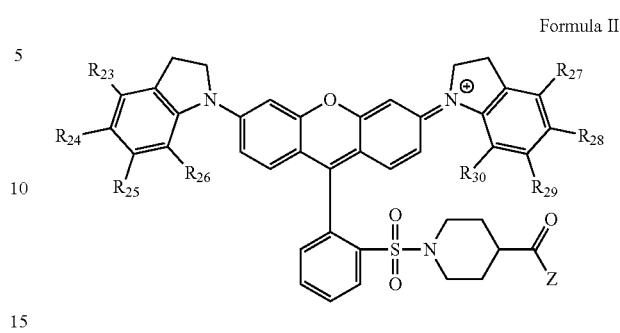

wherein each of $R_{23}$, $R_{24}$, $R_{25}$, $R_{26}$, $R_{27}$, Res, $R_{29}$, and $R_{30}$ is the same or different and is independently selected from either H or $SO_3$;

Z is OR, where R is H or alkyl, or NH-L, where L is

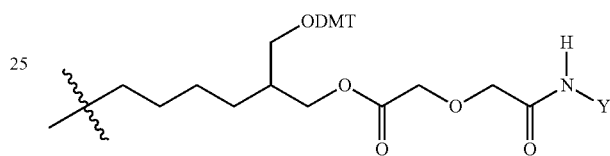

and Y is either H or a linkage to a solid support; and c) an oligonucleotide linker joining the dye and the quencher.

Clause 2. The probe of clause 1, wherein:
$R_5$, $R_6$, $R_9$, and $R_{10}$ are $SO_3$;
$R_7$ and $R_8$ are H;
$R_4$, $R_{13}$, and $R_{14}$ are methyl;
$R_2$ and $R_{12}$ are $SO_3$;
m, o, and p are 3; and n is 2.

Clause 3. The probe of clause 1, wherein:
$R_{10}$ is $SO_3$;
$R_5$, $R_6$, $R_7$, $R_8$, and $R_9$ are H;
$R_4$, $R_{13}$, and $R_{14}$ are methyl;
$R_{12}$ is H;
$R_2$ is $SO_3$;
m and o are 3; and n and p are 2.

Clause 4. The probe of clause 1, wherein:
$R_{10}$ is $SO_3$;
$R_5$, $R_6$, $R_7$, $R_8$, and $R_9$ are H;
$R_4$, $R_{13}$, and $R_{14}$ are methyl;
$R_2$ and Rig are $SO_3$;
m, o, and p are 3; and n is 2.

Clause 5. The probe of clause 1, wherein:
$R_9$ and $R_{10}$ are $SO_3$;
$R_5$, $R_6$, $R_7$, and $R_8$ are H;
$R_4$, $R_{13}$, and $R_{14}$ are methyl;
$R_{12}$ is H;
$R_2$ is $SO_3$;
m and o are 3; and n and p are 2.

Clause 6. The probe of clause 1, wherein:
$R_9$ and $R_{10}$ are $SO_3$;
$R_5$, $R_6$, $R_7$, and $R_8$ are H;
$R_4$, $R_{13}$, and $R_{14}$ are methyl;
$R_2$ and $R_{12}$ are $SO_3$;
m, o, and p are 3; and n is 2.

Clause 7. The probe of clause 1, wherein:

$R_5$, $R_6$, $R_7$, $R_8$, $R_9$, and $R_{10}$ are H;

$R_4$, $R_{13}$, and $R_{14}$ are methyl;

$R_2$ and $R_{12}$ are H;

m and p are 1; n is 2; and o is 3.

Clause 8. The probe of clause 1, wherein:

$R_{15}$, $R_{16}$, $R_{17}$, $R_{18}$, $R_{19}$, $R_{20}$, $R_{21}$, and $R_{22}$ are H;

$R_4$, $R_{13}$, and $R_{14}$ are methyl;

$R_2$ and $R_{12}$ are H;

m and p are 1; n is 2; and o is 3.

Clause 9. The probe of clause 1, wherein:

$R_{17}$ and $R_{18}$ are $SO_3$;

$R_{15}$, $R_{16}$, $R_{19}$, $R_{20}$, $R_{21}$, and $R_{22}$ are H;

$R_4$, $R_{13}$, and $R_{14}$ are methyl;

$R_2$ and Rig are $SO_3$;

m, o, and p are 3; and n is 2.

Clause 10. The probe of clause 1, wherein:

$R_5$, $R_6$, $R_9$, and $R_{10}$ are $SO_3$;

$R_7$ and $R_8$ are H;

$R_4$, $R_{13}$, and $R_{14}$ are methyl;

$R_3$ is —C-benzoate;

$R_2$ is $SO_3$ and $R_{12}$ is H;

m is 3; p is 1; and n is 2.

Clause 11. The probe of clause 1, wherein each of $R_{23}$, $R_{25}$, $R_{26}$, $R_{27}$, $R_{29}$, and $R_{30}$ is H and each of $R_{24}$ and $R_{28}$ is $SO_3$.

Clause 12. The probe of clause 1, wherein each of $R_{23}$, $R_{24}$, $R_{25}$, $R_{26}$, $R_{27}$, $R_{28}$, $R_{29}$, and $R_{30}$ is H.

Clause 13. The probe of clause 1, wherein Z is $CO_2R$, where R is NH-L, L being

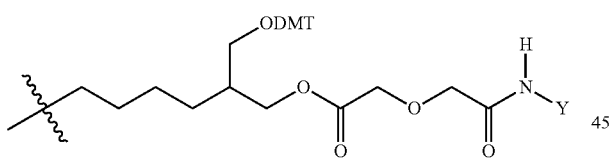

and Y being the linkage to the solid support.

Clause 14. A method of detecting or quantifying a target nucleic acid molecule in a sample by polymerase chain reaction (PCR), the method comprising:

(i) contacting the sample comprising one or more target nucleic acid molecules with a) at least one probe having a sequence that is at least partially complementary to the target nucleic acid molecule, where the at least one probe undergoes a detectable change in fluorescence upon amplification of the one or more target nucleic acid molecules; and with b) at least one oligonucleotide primer pair;

(ii) incubating the mixture of step (i) with a DNA polymerase under conditions sufficient to amplify one or more target nucleic acid molecules; and (iii) detecting the presence or absence or quantifying the amount of the amplified target nucleic acid molecules by measuring fluorescence of the probe, wherein the probe comprises a product of conjugation of:

a) a dye having a general Formula Ia, Formula Ib, Formula Ic, or Formula Id

Formula Ia

Formula Ib

Formula Ic

Formula Id wherein each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;

each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;

each of $R_2$ and $R_{12}$ is the same or different and is selected from the group consisting of H and $SO_3$;

X is selected from the group consisting of —OH, —SH, —$NH_2$, —NH—$NH_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, $NH(CH_2CH_2O)_zCH_2CH_2N_3$, —NR-L-NH—CO—$CH_2$—I, and an azide ($N_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive;

b) a quencher having general Formula II

Formula II

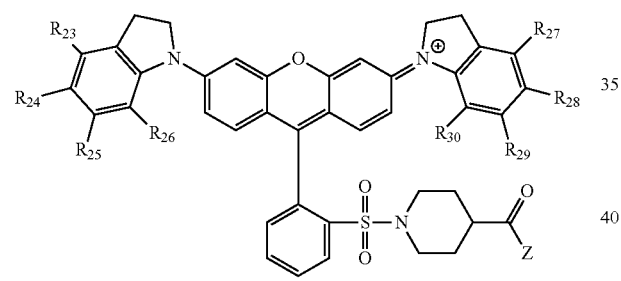

wherein
each of $R_{23}$, $R_{24}$, $R_{25}$, $R_{26}$, $R_{27}$, $R_{28}$, $R_{29}$, and $R_{30}$ is the same or different and is
independently selected from either H or $SO_3$;
Z is OR, where R is H or alkyl, or NH-L, where L is and Y is either H or a linkage to a solid support; and
c) at least one oligonucleotide linker joining the dye and the quencher.

Clause 15. The method of clause 14, wherein the PCR is real-time or quantitative PCR (qPCR).

Clause 16. The method of clause 14 or clause 15, wherein the polymerase is a Taq polymerase.

Clause 17. The method of any one of the preceding clauses, wherein the probe is a hydrolysis probe.

Clause 18. The method of any one of the preceding clauses, wherein the probe is a TaqMan probe.

Clause 19. The method of any one of the preceding clauses, wherein the target nucleic acid comprises a mutation.

Clause 20. The method of any one of the preceding clauses, wherein the method is used for detection of a rare allele or SNP.

Clause 21. A kit for polymerase chain reaction (PCR), the kit comprising:

a probe comprising a product of conjugation of:

a) a dye having a general Formula Ia, Formula Ib, Formula Ic, or Formula Id

Formula Ia

Formula Ib

Formula Ic

Formula Id

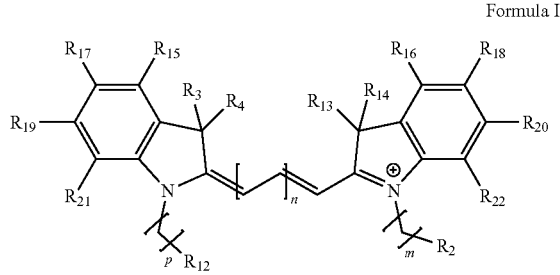

wherein
each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;
each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;
each of $R_2$ and $R_{12}$ is the same or different and is selected from the group consisting of H and $SO_3$;
X is selected from the group consisting of —OH, —SH, —$NH_2$, —NH—$NH_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, $NH(CH_2CH_2O)_zCH_2CH_2N_3$, —NR-L-NH—CO—$CH_2$—I, and an azide ($N_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom;
Kat is a number of $Na^+$, $K^+$, $Ca^{2+}$, ammonia, or other cation(s) needed to compensate the negative charge brought by the cyanine;
m is an integer from 0 to 5 inclusive; n is an integer from 1 to 3 inclusive; o is an integer from 0 to 12 inclusive; and p is an integer from 0 to 5 inclusive;
b) a quencher having general Formula II Formula II

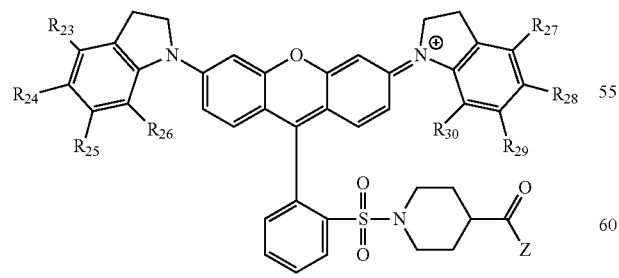

wherein
each of $R_{23}$, $R_{24}$, $R_{25}$, $R_{26}$, $R_{27}$, $R_{28}$, $R_{29}$, and $R_{30}$ is the same or different and is independently selected from either H or $SO_3$;

Z is OR, where R is H or alkyl, or NH-L, where L is

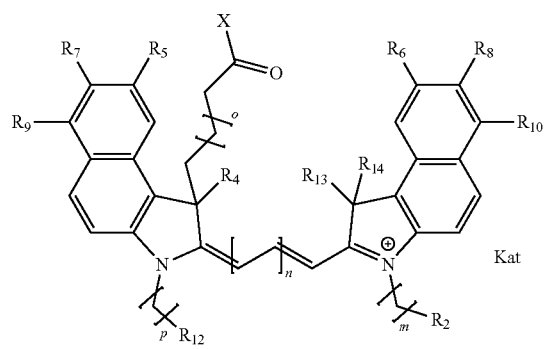

and Y is either H or a linkage to a solid support; and
c) at least one oligonucleotide linker joining the dye and the quencher; and
one or more of the following: a buffering agent, a purification medium, the target, an organic solvent, an enzyme, and an enzyme inhibitor.

Clause 22. The kit of clause 21, wherein the PCR is real-time or quantitative PCR (qPCR).

Clause 23. The kit of clause 21 or clause 22, further comprising instructions for conducting the real-time or quantitative PCR (qPCR).

Clause 24. The kit of any one of the preceding clauses, wherein the components are packaged in separate containers.

Clause 25. The kit of any one of the preceding clauses, wherein two or more components are packaged together as a master mix.

Clause 26. A kit comprising at least one a dye having a general Formula Ia, Formula Ib, Formula Ic, or Formula Id Formula Ia

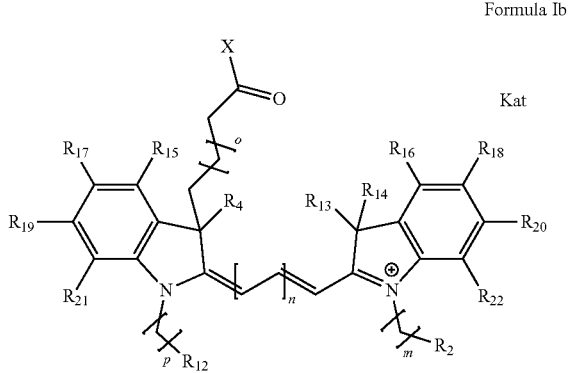

Formula Ib

Formula Ic

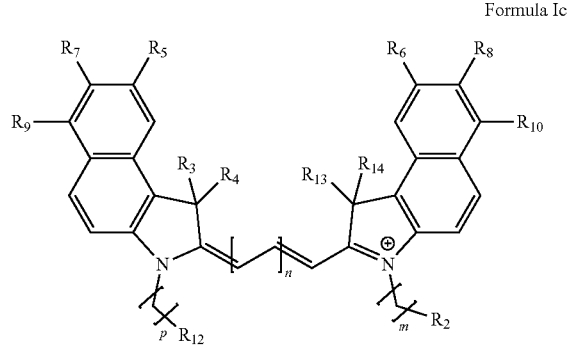

Formula Id

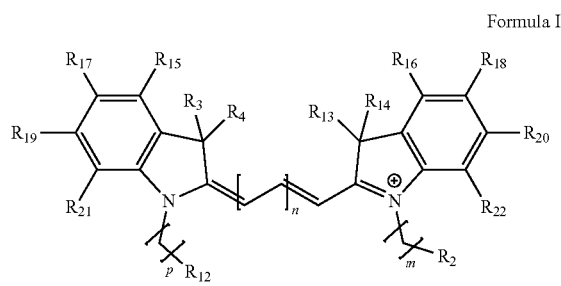

wherein
each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;

each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;

each of $R_2$ and $R_{12}$ is the same or different and is selected from the group consisting of H and $SO_3$;

X is selected from the group consisting of —OH, —SH, —$NH_2$, —NH—$NH_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2H$, —NR-L-CO—NHS, —NR-L-CO-STP, —NR-L-CO-TFP, —NR-L-CO-benzotriazole, —NR-L-CHO, —NR-L-maleimide, $NH(CH_2CH_2O)_zCH_2CH_2N_3$, —NR-L-NH—CO—$CH_2$—I, and an azide ($N_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom;

Kat is a number of $Na^+$, $K^+$, $Ca^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive; and at least one quencher having general Formula II

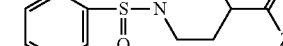

Formula II wherein
each of $R_{23}$, $R_{24}$, $R_{25}$, $R_{26}$, $R_{27}$, $R_{28}$, $R_{29}$, and $R_{30}$ is the same or different and is independently selected from either H or $SO_3$;

Z is OR, where R is H or alkyl, or NH-L, where L is and Y is either H or a linkage to a solid support.

Clause 27. The kit of clause 26, further comprising additional components for conjugating the at least one dye and the at least one quencher to an oligonucleotide.

Clause 28. The kit of clause 26 or clause 27, further comprising instructions for conjugating the at least one dye and the at least one quencher to an oligonucleotide.

Clause 29. The kit of any one of the preceding clauses, wherein the components are packaged in separate containers.

Clause 30. The probe of any one of the preceding clauses, wherein the azide-containing group comprises an aliphatic linker with a terminal azide.

Clause 31. The probe of any one of the preceding clauses, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

Clause 32. The method of any one of the preceding clauses, wherein the azide-containing group comprises an aliphatic linker with a terminal azide.

Clause 33. The method of any one of the preceding clauses, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

Clause 34. The kit of any one of the preceding clauses, wherein the azide-containing group comprises an aliphatic linker with a terminal azide.

Clause 35. The kit of any one of the preceding clauses, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

Clause 36. The kit of any one of the preceding clauses, wherein the azide-containing group comprises an aliphatic linker with a terminal azide.

Clause 37. The kit of any one of the preceding clauses, wherein the aliphatic linker with a terminal azide is selected from NH—CH$_2$—CH$_2$—CH$_2$—N$_3$ or NH$_2$—CH$_2$—CH$_2$—O—CH$_2$—CH$_2$—O—CH$_2$—CH$_2$—O—CH$_2$—CH$_2$—N$_3$.

The invention claimed is:

1. A probe comprising a product of conjugation of:
   a) a dye having a general Formula Ia, Formula Ib, Formula Ic, or Formula Id

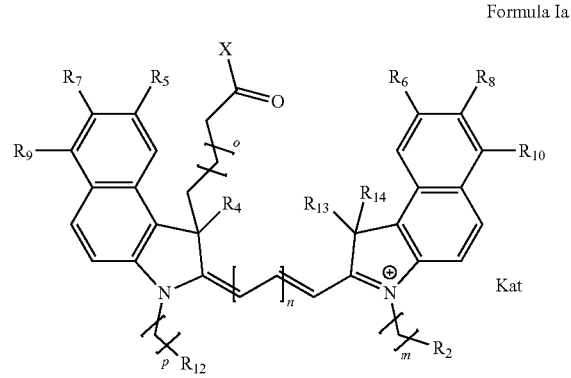

wherein each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal SO$_3$, a benzyl, and a substituted benzyl, where the substituted benzyl comprises at least one carboxy group, at least one sulfonate group, —F, —Cl, —Br, or a combination thereof;

each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and SO$_3$;

each of $R_2$ and $R_{12}$ is the same or different and is selected from the group consisting of H and SO$_3$;

X is selected from the group consisting of —OH, —SH, —NH$_2$, —NH—NH$_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NH(CH$_2$CH$_2$O)$_z$CH$_2$CH$_2$N$_3$, —NR-L-NH—CO—CH$_2$—I, and an azide (N$_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom;

Kat is a number of Na$^+$, K$^+$, Ca$^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive;

b) a quencher having general Formula II

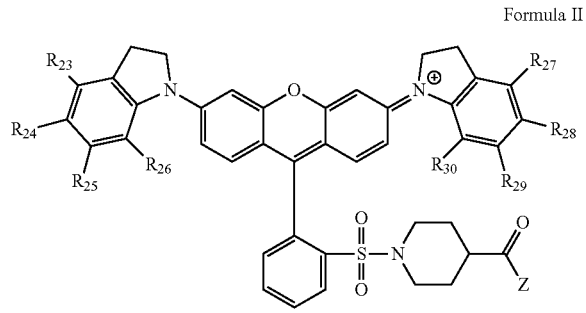

wherein each of $R_{23}$, $R_{24}$, $R_{25}$, $R_{26}$, $R_{27}$, $R_{28}$, $R_{29}$, and $R_{30}$ is the same or different and is independently selected from either H or SO$_3$;

Z is OR, where R is alkyl, or Z is NH-L, where L is

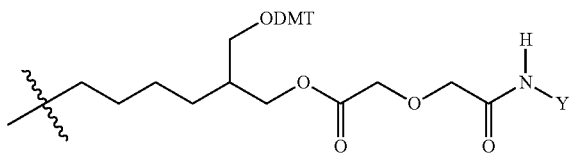

and Y is either H or a linkage to a solid support; and
c) an oligonucleotide linker joining the dye and the quencher, wherein the dye is covalently joined to a first nucleotide of the oligonucleotide and the quencher is covalently joined to a second, different nucleotide of the oligonucleotide.

2. The probe of claim 1, wherein:
$R_5$, $R_6$, $R_9$, and $R_{10}$ are $SO_3$;
$R_7$ and $R_8$ are H;
$R_4$, $R_{13}$, and $R_{14}$ are methyl;
$R_2$ and $R_{12}$ are $SO_3$;
m, o, and p are 3; and n is 2.

3. The probe of claim 1, wherein:
$R_{10}$ is $SO_3$;
$R_5$, $R_6$, $R_7$, $R_8$, and $R_9$ are H;
$R_4$, $R_{13}$, and $R_{14}$ are methyl;
$R_{12}$ is H;
$R_2$ is $SO_3$;
m and o are 3; and n and p are 2.

4. The probe of claim 1, wherein:
$R_{10}$ is $SO_3$;
$R_5$, $R_6$, $R_7$, $R_8$, and $R_9$ are H;
$R_4$, $R_{13}$, and $R_{14}$ are methyl;
$R_2$ and $R_{12}$ are $SO_3$;
m, o, and p are 3; and n is 2.

5. The probe of claim 1, wherein:
$R_9$ and $R_{10}$ are $SO_3$;
$R_5$, $R_6$, $R_7$, and $R_8$ are H;
$R_4$, $R_{13}$, and $R_{14}$ are methyl;
$R_{12}$ is H;
$R_2$ is $SO_3$;
m and o are 3; and n and p are 2.

6. The probe of claim 1, wherein:
$R_9$ and $R_{10}$ are $SO_3$;
$R_5$, $R_6$, $R_7$, and $R_8$ are H;
$R_4$, $R_{13}$, and $R_{14}$ are methyl;
$R_2$ and $R_{12}$ are $SO_3$;
m, o, and p are 3; and n is 2.

7. The probe of claim 1, wherein:
$R_5$, $R_6$, $R_7$, $R_8$, $R_9$, and $R_{10}$ are H;
$R_4$, $R_{13}$, and $R_{14}$ are methyl;
$R_2$ and $R_{12}$ are H;
m and p are 1; n is 2; and o is 3.

8. The probe of claim 1, wherein:
$R_{15}$, $R_{16}$, $R_{17}$, $R_{18}$, $R_{19}$, $R_{20}$, $R_{21}$, and $R_{22}$ are H;
$R_4$, $R_{13}$, and $R_{14}$ are methyl;
$R_2$ and $R_{12}$ are H;
m and p are 1; n is 2; and o is 3.

9. The probe of claim 1, wherein:
$R_{17}$ and $R_{18}$ are $SO_3$;
$R_{15}$, $R_{16}$, $R_{19}$, $R_{20}$, $R_{21}$, and $R_{22}$ are H;
$R_4$, $R_{13}$, and $R_{14}$ are methyl;
$R_2$ and $R_{12}$ are $SO_3$;
m, o, and p are 3; and n is 2.

10. The probe of claim 1, wherein:
$R_5$, $R_6$, $R_9$, and $R_{10}$ are $SO_3$;
$R_7$ and $R_8$ are H;
$R_4$, $R_{13}$, and $R_{14}$ are methyl;
$R_3$ is —C-benzoate;
$R_2$ is $SO_3$ and $R_{12}$ is H;
m is 3; p is 1; and n is 2.

11. The probe of claim 1, wherein each of $R_{23}$, $R_{25}$, $R_{26}$, $R_{27}$, $R_{29}$, and $R_{30}$ is H and each of $R_{24}$ and $R_{28}$ is $SO_3$.

12. The probe of claim 1, wherein each of $R_{23}$, $R_{24}$, $R_{25}$, $R_{26}$, $R_{27}$, $R_{28}$, $R_{29}$, and $R_{30}$ is H.

13. The probe of claim 1, wherein Z is NH-L, L being

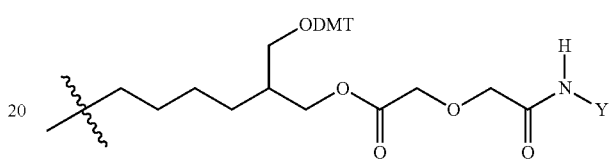

and Y being the linkage to the solid support.

14. A method of detecting or quantifying a target nucleic acid molecule in a sample by polymerase chain reaction (PCR), the method comprising:
(i) contacting the sample comprising one or more target nucleic acid molecules with a) at least one probe having a sequence that is at least partially complementary to the target nucleic acid molecule, where the at least one probe undergoes a detectable change in fluorescence upon amplification of the one or more target nucleic acid molecules; and with b) at least one oligonucleotide primer pair;
(ii) incubating the mixture of step (i) with a DNA polymerase under conditions sufficient to amplify one or more target nucleic acid molecules; and
(iii) detecting the presence or absence or quantifying the amount of the amplified target nucleic acid molecules by measuring fluorescence of the probe, wherein the probe comprises a product of conjugation of:
a) a dye having a general Formula Ia, Formula Ib, Formula Ic, or Formula Id Formula Ia

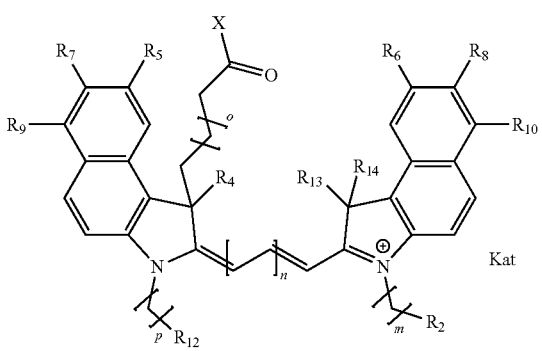

-continued

Formula Ib

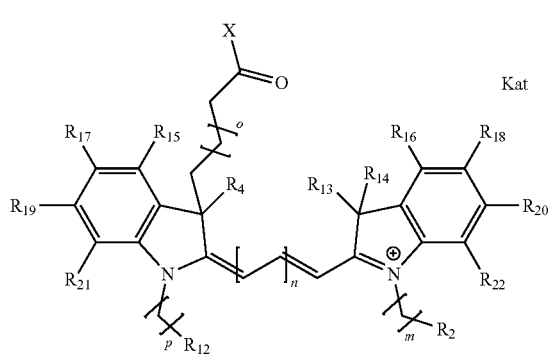

Formula Ic

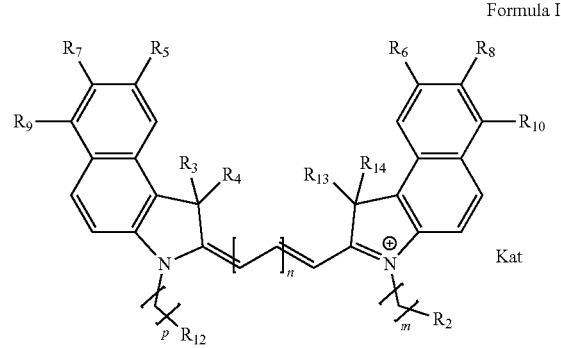

Formula Id

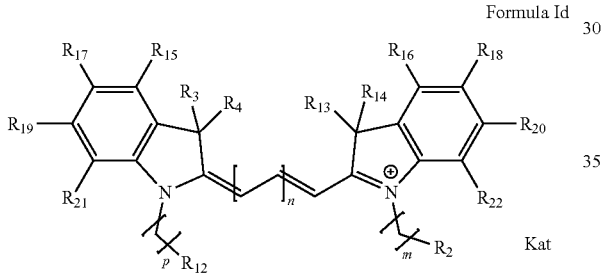

wherein
each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;
each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;
each of $R_2$ and $R_{12}$ is the same or different and is selected from the group consisting of H and $SO_3$;
X is selected from the group consisting of —OH, —SH, —NH$_2$, —NH—NH$_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NH(CH$_2$CH$_2$O)$_z$CH$_2$CH$_2$N$_3$, —NR-L-NH—CO—CH$_2$—I, and an azide (N$_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom;

Kat is a number of Na$^+$, K$^+$, Ca$^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive;

b) a quencher having general Formula II

Formula II

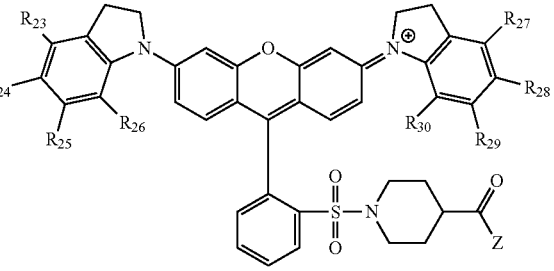

wherein
each of $R_{23}$, $R_{24}$, $R_{25}$, $R_{26}$, $R_{27}$, $R_{28}$, $R_{29}$, and $R_{30}$ is the same or different and is independently selected from either H or $SO_3$;
Z is OR, where R is alkyl, or Z is NH-L, where L is

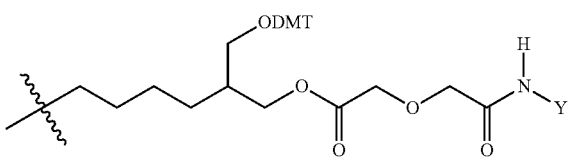

and Y is either H or a linkage to a solid support; and c) at least one oligonucleotide linker joining the dye and the quencher, wherein the dye is covalently joined to a first nucleotide of the oligonucleotide and the quencher is covalently joined to a second, different nucleotide of the oligonucleotide.

15. The method of claim 14, wherein the PCR is real-time or quantitative PCR (qPCR).

16. The method of claim 14, wherein the polymerase is a Taq polymerase.

17. The method of claim 14, wherein the probe is a hydrolysis probe.

18. The method of claim 14, wherein the probe is a TaqMan probe.

19. The method of claim 14, wherein the target nucleic acid comprises a mutation.

20. The method of claim 14, wherein the method is used for detection of a rare allele or SNP.

21. A kit for polymerase chain reaction (PCR), the kit comprising:
a probe comprising a product of conjugation of:
a) a dye having a general Formula Ia, Formula Ib, Formula Ic, or Formula Id

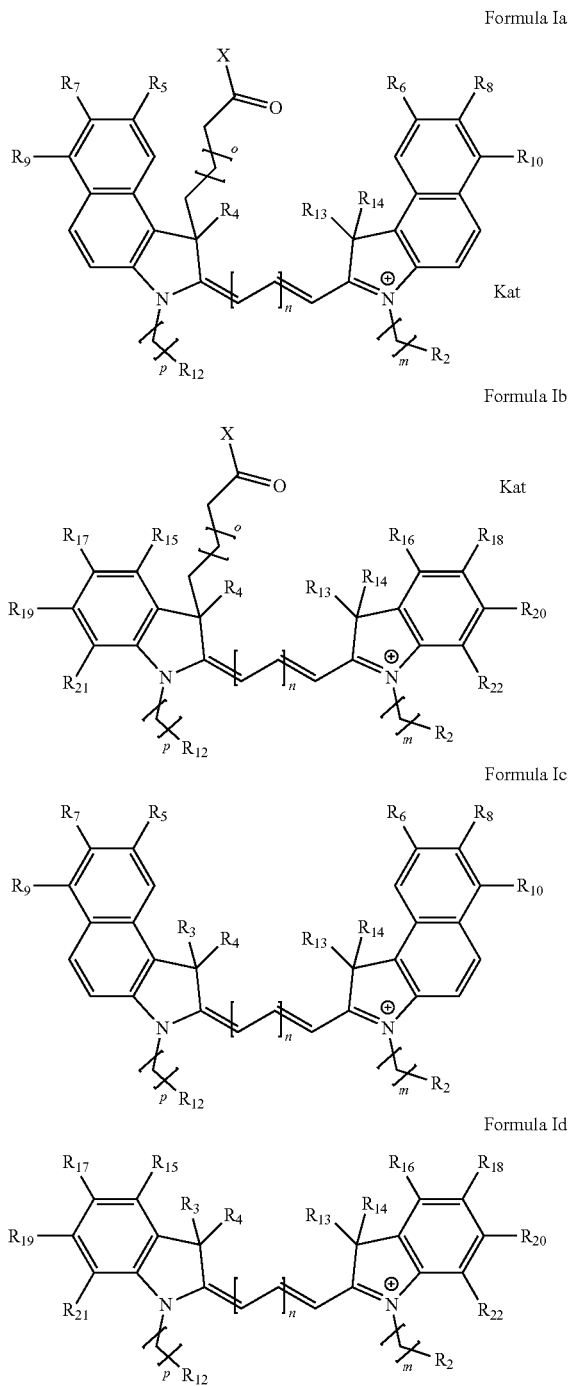

wherein
each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;

each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;

each of $R_2$ and $R_{12}$ is the same or different and is selected from the group consisting of H and $SO_3$;

X is selected from the group consisting of —OH, —SH, —NH$_2$, —NH—NH$_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, NH(CH$_2$CH$_2$O)$_z$CH$_2$CH$_2$N$_3$, —NR-L-NH—CO—CH$_2$—I, and an azide (N$_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom;

Kat is a number of Na$^+$, K$^+$, Ca$^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive;

b) a quencher having general Formula II

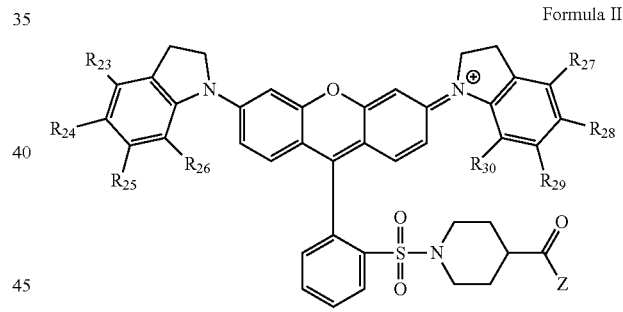

wherein
each of $R_{23}$, $R_{24}$, $R_{25}$, $R_{26}$, $R_{27}$, $R_{28}$, $R_{29}$, and $R_{30}$ is the same or different and is independently selected from either H or $SO_3$;

Z is OR, where R is alkyl, or Z is NH-L, where L is

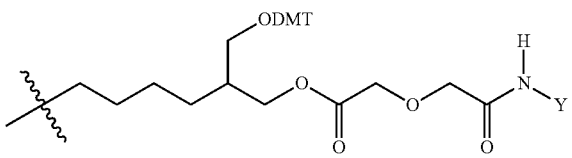

and Y is either H or a linkage to a solid support; and
c) at least one oligonucleotide linker joining the dye and the quencher, wherein the dye is covalently joined to a first nucleotide of the oligonucleotide and the quencher is covalently joined to a second, different nucleotide of the oligonucleotide; and one or more of the following: a buffering agent, a purification medium, the target, an organic solvent, an enzyme, and an enzyme inhibitor.

22. The kit of claim 21, wherein the PCR is real-time or quantitative PCR (qPCR).

23. The kit of claim 21, further comprising instructions for conducting the real-time or quantitative PCR (qPCR).

24. The kit of claim 21, wherein the components are packaged in separate containers.

25. The kit of claim 21, wherein two or more components are packaged together as a master mix.

26. A kit comprising at least one a dye having a general Formula Ia, Formula Ib, Formula Ic, or Formula Id Formula Ia
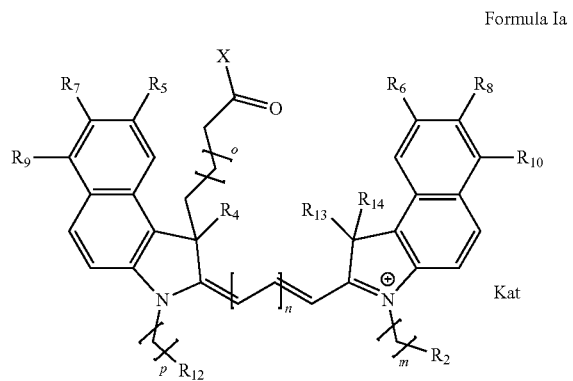

Formula Ib
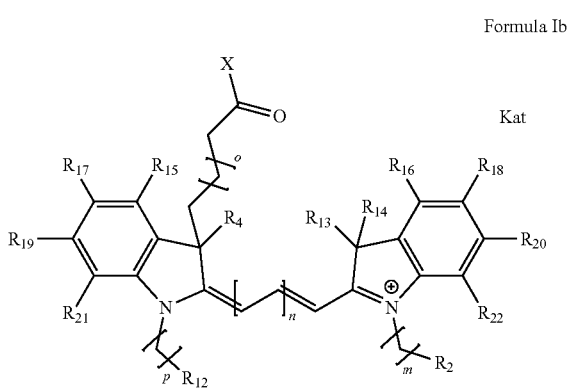

Formula Ic
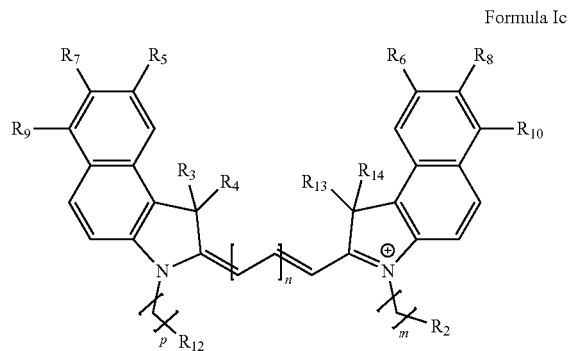

-continued

Formula Id
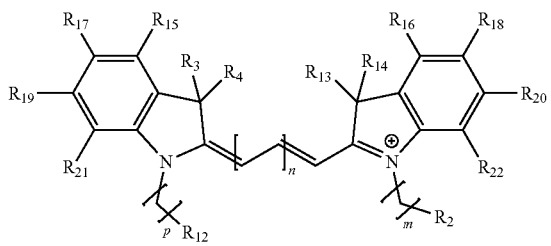

wherein
each of $R_4$, $R_{13}$, and $R_{14}$, and $R_3$ when present, is the same or different and is selected from the group consisting of H, an aliphatic, a heteroaliphatic, a sulfoalkyl, a heteroaliphatic with terminal $SO_3$, a benzyl, and a substituted benzyl, where the substituted benzyl comprises at least one carboxy group, at least one sulfonate group, —F, —Cl, —Br, or a combination thereof;

each of $R_5$, $R_6$, $R_7$, $R_8$, $R_9$, $R_{10}$, $R_{15}$, $R_{16}$, $R_{17}$, $R_{18}$, $R_{19}$, $R_{20}$, $R_{21}$, and $R_{22}$ is the same or different and is selected from the group consisting of H and $SO_3$;

each of $R_2$ and $R_{12}$ is the same or different and is selected from the group consisting of H and $SO_3$;

X is selected from the group consisting of —OH, —SH, —NH$_2$, —NH—NH$_2$, —F, —Cl, —Br, I, —O—NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, NH(CH$_2$CH$_2$O)$_z$CH$_2$CH$_2$N$_3$, —NR-L-NH—CO—CH$_2$—I, and an azide (N$_3$)-containing group, where R is —H or an aliphatic or heteroaliphatic group, z is an integer from 1 to 5 inclusive, and L is selected from the group consisting of a divalent linear, crossed, or cyclic alkyl group optionally substituted by at least one oxygen atom and/or sulfur atom;

Kat is a number of Na$^+$, K$^+$, Ca$^{2+}$, ammonia, or other cation(s) needed to compensate the negative charge brought by the cyanine;

m is an integer from 0 to 5 inclusive; n is an integer from 1 to 3 inclusive; o is an integer from 0 to 12 inclusive; and p is an integer from 0 to 5 inclusive; and at least one quencher having general Formula II Formula II
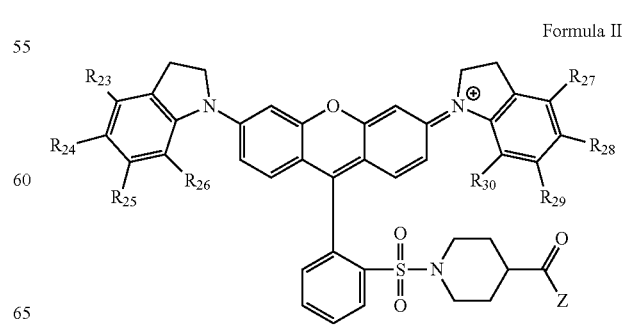

wherein
each of $R_{23}$, $R_{24}$, $R_{25}$, $R_{26}$, $R_{27}$, $R_{28}$, $R_{29}$, and $R_{30}$ is the same or different and is independently selected from either H or $SO_3$;

Z is OR, where R is alkyl, or Z is NH-L, where L is

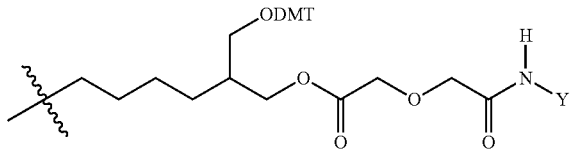

and Y is either H or a linkage to a solid support.

27. The kit of claim 26, further comprising additional components for conjugating the at least one dye and the at least one quencher to an oligonucleotide such that the dye is covalently joined to a first nucleotide of the oligonucleotide and the quencher is covalently joined to a second, different nucleotide of the oligonucleotide.

28. The kit of claim 27, further comprising instructions for conjugating the at least one dye and the at least one quencher to an oligonucleotide such that the dye is covalently joined to a first nucleotide of the oligonucleotide and the quencher is covalently joined to a second, different nucleotide of the oligonucleotide.

29. The kit of claim 26, wherein the components are packaged in separate containers.

30. The probe of claim 1, wherein the azide-containing group comprises an aliphatic linker with a terminal azide.

31. The probe of claim 30, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

32. The method of claim 14, wherein the azide-containing group comprises an aliphatic linker with a terminal azide.

33. The method of claim 32, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

34. The kit of claim 21, wherein the azide-containing group comprises an aliphatic linker with a terminal azide.

35. The kit of claim 34, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

36. The kit of claim 26, wherein the azide-containing group comprises an aliphatic linker with a terminal azide.

37. The kit of claim 36, wherein the aliphatic linker with a terminal azide is selected from NH—$CH_2$—$CH_2$—$CH_2$—$N_3$ or $NH_2$—$CH_2$—$CH_2$—O—$CH_2$—$CH_2$—O—$CH_2$—$CH_2$—O—$CH_2$—$CH_2$—$N_3$.

* * * * *

UNITED STATES PATENT AND TRADEMARK OFFICE
CERTIFICATE OF CORRECTION

PATENT NO. : 11,535,885 B2
APPLICATION NO. : 15/733557
DATED : December 27, 2022
INVENTOR(S) : Khairuzzaman Bashar Mullah et al.

It is certified that error appears in the above-identified patent and that said Letters Patent is hereby corrected as shown below:

In the Claims

In Column 70, Claim 10, Line 3, delete "Rig" and insert -- R12 --, therefor.

Signed and Sealed this
Twenty-first Day of February, 2023

Katherine Kelly Vidal
*Director of the United States Patent and Trademark Office*